(12) United States Patent
Munakata et al.

(10) Patent No.: US 11,624,048 B2
(45) Date of Patent: Apr. 11, 2023

(54) SWITCHING VALVE AND SUCTION-DISCHARGE DEVICE INCLUDING THE SAME

(71) Applicants: RORZE LIFESCIENCE INC., Tsukuba (JP); RORZE CORPORATION, Fukuyama (JP)

(72) Inventors: Teruyoshi Munakata, Tsukuba (JP); Atsuyoshi Tanioka, Fukuyama (JP); Yukito Yamasaki, Tsukuba (JP)

(73) Assignees: RORZE LIFESCIENCE INC., Tsukuba (JP); RORZE CORPORATION, Fukuyama (JP)

( * ) Notice: Subject to any disclaimer, the term of this patent is extended or adjusted under 35 U.S.C. 154(b) by 401 days.

(21) Appl. No.: 17/092,869

(22) Filed: Nov. 9, 2020

(65) Prior Publication Data
US 2021/0054329 A1      Feb. 25, 2021

Related U.S. Application Data

(63) Continuation of application No. 15/918,642, filed on Mar. 12, 2018, now Pat. No. 10,865,375, which is a
(Continued)

(30) Foreign Application Priority Data

Sep. 14, 2015 (JP) ............................. JP2015-180298

(51) Int. Cl.
*C12M 1/00* (2006.01)
*F16K 7/06* (2006.01)
(Continued)

(52) U.S. Cl.
CPC ................ *C12M 29/14* (2013.01); *B01J 4/02* (2013.01); *C12M 1/00* (2013.01); *C12M 33/04* (2013.01);
(Continued)

(58) Field of Classification Search
None
See application file for complete search history.

(56) References Cited

U.S. PATENT DOCUMENTS 3,227,315 A * 1/1966 Wain ...................... G01F 11/00
  222/64
3,960,149 A    6/1976 Bujan
(Continued)

FOREIGN PATENT DOCUMENTS

CN      1319736 A    10/2001
CN      1491121 A     4/2004
(Continued)

OTHER PUBLICATIONS

China National Intellectual Property Administration, "Search Report for Chinese Patent Application No. 202010393152.8," dated Oct. 28, 2021.
(Continued)

*Primary Examiner* — Holly Kipouros
(74) *Attorney, Agent, or Firm* — Manabu Kanesaka

(57) ABSTRACT

A switching valve includes a rotor having a pair of rollers rotatably mounted on both ends thereof, a rotor drive unit rotationally driving the rotor, a pair of pressing members, each being provided at a position where each of the pair of pressing members cooperates with each of the pair of rollers outside a revolution orbit of each of the pair of rollers revolving by rotation of the rotor, and a pair of tubes, each being disposed between the revolution orbit of each of the pair of rollers and each of the pair of pressing members. A rotation center axis of the rotor is disposed on a straight line connecting centers of rotation of the pair of rollers, and each pressing member has the pair of pressing areas symmetrical with respect to a straight line passing through the center of rotation of the rotor and extending a vertical direction.

6 Claims, 16 Drawing Sheets

Related U.S. Application Data continuation of application No. PCT/JP2016/076366, filed on Sep. 8, 2016.

(51) Int. Cl.
  *B01J 4/02* (2006.01)
  *G01N 1/00* (2006.01)
  *G01N 35/10* (2006.01)
  *C12M 1/26* (2006.01)

(52) U.S. Cl.
  CPC .............. *F16K 7/06* (2013.01); *G01N 1/00* (2013.01); *G01N 35/10* (2013.01)

(56) References Cited

U.S. PATENT DOCUMENTS

| | | | |
|---|---|---|---|
| 4,269,333 A * | 5/1981 | Nakai | B67D 3/00 222/506 |
| 5,746,251 A * | 5/1998 | Bullard | F16K 11/076 251/6 |
| 2001/0043886 A1 | 11/2001 | Park et al. | |
| 2003/0006193 A1 | 1/2003 | Ikeda et al. | |
| 2004/0048393 A1 | 3/2004 | Colin et al. | |
| 2005/0255426 A1 * | 11/2005 | Mariaulle | F16K 11/027 433/84 |
| 2007/0181835 A1 | 8/2007 | Hanada | |
| 2010/0114024 A1 | 5/2010 | Evans et al. | |
| 2011/0124093 A1 | 5/2011 | Yamashita | |
| 2011/0152682 A1 | 6/2011 | Evans et al. | |
| 2011/0160581 A1 | 6/2011 | Evans et al. | |
| 2012/0238965 A1 | 9/2012 | Chang | |
| 2013/0118619 A1 | 5/2013 | Loth et al. | |
| 2014/0120610 A1 | 5/2014 | Yamashita et al. | |
| 2015/0004034 A1 | 1/2015 | Hansen | |
| 2015/0297830 A1 | 10/2015 | Okiyama | |

FOREIGN PATENT DOCUMENTS

| | | |
|---|---|---|
| CN | 1894525 A | 1/2007 |
| CN | 102046770 A | 5/2011 |
| CN | 102271733 A | 12/2011 |
| CN | 103597067 A | 2/2014 |
| CN | 104066986 A | 9/2014 |
| CN | 104507528 A | 4/2015 |
| FR | 2291442 A1 | 6/1976 |
| JP | H10-238472 A | 9/1998 |

OTHER PUBLICATIONS

China Patent Office, "Office Action for Chinese Patent Application No. 202010393152.8," dated Aug. 3, 2021.

Zhongyu, Z, "Pressure regulation-Overflow compound air valve," Harbin Mechanical Research Laboratories, Dec. 31, 1983, p. 41-44.

* cited by examiner

SWITCHING VALVE AND SUCTION-DISCHARGE DEVICE INCLUDING THE SAME

CROSS-REFERENCE TO RELATED APPLICATION

This is a continuation application of Ser. No. 15/918,642 filed on Mar. 12, 2018, which is a continuation application of PCT International Application No. PCT/JP2016/076366 filed on Sep. 8, 2016, the disclosure of which is incorporated herein.

TECHNICAL FIELD

The present invention relates to a pump module that is mounted on a dispensing machine or a culture medium replacement apparatus, and more particularly to a pump module that can supply liquid in a sterile state and a replaceable suction-discharge assembly that is applied to the pump module. Further, the invention relates to an automatic culture medium replacement apparatus, a dispensing apparatus, and an automatic culture system on which the pump module is mounted.

BACKGROUND ART

A dispensing apparatus is known as a device that transfers liquid, such as a specimen or a reagent, used for tests or analysis performed in a biotechnology field. Further, a culture medium replacement apparatus is known as an apparatus that replaces culture liquid, such as a culture medium, at a predetermined timing in a cell culture that is performed in a regenerative medicine field for a long time period. Each of these apparatuses includes a suction-discharge device that sucks and discharges a liquid sample, such as cell suspension or culture liquid.

Here, the suction-discharge device included in the dispensing apparatus and the culture medium replacement apparatus in the related art will be described below. In a dispensing apparatus disclosed in Patent Document 1, a tubing pump PM, which rotates a pressing roller by a motor and continuously squeezes a soft tube by the pressing roller to transfer fluid present in the tube in a predetermined direction, is used as a pump for sucking and discharging a sample (see FIG. 1). The tubing pump PM is adapted to suck a sample, which is stored in a receiving vessel BT, and to discharge the sample to dispensing heads h1 and h2 by being activated. Accordingly, the supply of a sample, which has been manually performed until now, could be completed in a relatively short time. However, the tubing pump could continuously supply a large amount of sample, but it was difficult for the tubing pump to accurately discharge a sample. Further, since the soft tube is continuously squeezed by the pressing roller, the soft tube allowing fluid to flow deteriorates. For this reason, there is a trouble that the accuracy of the amount of a sample to be discharged deteriorates. Furthermore, there is also a trouble that the inner wall of the deteriorated tube is separated and is mixed to a specimen together with a sample.

In contrast, a suction-discharge device disclosed in Patent Document 2 includes a syringe type syringe pump 1 (reference numerals disclosed in Patent Document 2 are applied as reference numerals of the respective portions, the same applies to the following paragraphs) as pump means. The suction-discharge device is adapted so that a sample is sucked when a plunger 1a of the syringe pump 1 is drawn from a cylinder 1b by pump drive means 7 and a sample is discharged when the plunger 1a is pushed into the cylinder 1b. Further, the suction-discharge device is adapted so that the suction/discharge directions of liquid can be switched by a switching valve 13 that is driven so as to be opened and closed by valve opening/closing means 27. Sample liquid, which is present in a sample vessel 9, can be sucked through water, which is filled in a tube 5, and can be discharged into a reaction tube 11 by the switching of the switching valve 13. Since the operations of the pump drive means 7 and the valve opening/closing means 27 are electrically controlled by a control device 31, predetermined liquid can be sucked and discharged to a predetermined place by a predetermined amount in accordance with a predetermined procedure.

CITATION LIST

Patent Document

Patent Document 1: JP 05-126690 A
Patent Document 2: JP 08-220106 A

SUMMARY OF THE INVENTION

Problems to be Solved by the Invention

An accurate amount of sample can be automatically sucked and discharged by the cited techniques, but there are following problems.

That is, even though the above-mentioned pump in the related art is used, there is a problem that dust, which is generated from the switching valve provided to switch the suction/discharge directions of a sample, is mixed to the sample and contaminates a specimen. Further, the suction-discharge device is regularly subjected to washing using sterilization liquid or treatment using autoclave to remove bacteria or contaminant entering from the external environment. However, since the switching valve allows a sample to flow in flow passages formed in the body and electrically activates a valve body provided in the body to switch the flow passages, the switching valve cannot be subjected to sterilization or treatment using autoclave. For this reason, there is a problem that bacteria or dust, which remains in the switching valve in which a sample flows, negatively affects the next culture. In addition, since the tube or the cylinder having been subjected to sterilization treatment is contaminated due to the adherence of bacteria or dust floating in the air when being installed again after sterilization treatment, there is also a problem that cell culture is negatively affected.

The invention has been made to solve the above-mentioned problems, and an object of the invention is to provide a switching valve that can effectively prevent dust or bacteria from entering, a suction-discharge device including the switching valve, a culture medium replacement apparatus and a dispensing apparatus including the suction-discharge device, and an automatic culture system including these apparatus. Further, an object of the invention is to provide a suction-discharge assembly that is applied to the suction-discharge device, is sterilely packed, and can be easily replaced.

Means for Solving Problem

To solve the problems, the invention provides a switching valve including: a rotor that includes a pair of rollers rotatably mounted on both ends thereof, a rotor drive unit that rotationally drives the rotor; a pair of pressing members that is provided at positions where the pressing members cooperate with the respective rollers outside a revolution orbit of the pair of rollers revolving by the rotation of the rotor; and a pair of tubes that are disposed between the revolution orbit of the rollers and the pair of pressing members, respectively. The pressing members are disposed so that a gap between each pressing member and the revolution orbit of each roller is gradually narrowed. Pressing areas where the respective rollers and the respective pressing members press the tubes are formed by the revolution of the rollers, and the respective pair of tubes are selectively blocked and opened from the outside by the pair of rollers and the pair of pressing members. According to the above-mentioned structure, the opening and blocking of the tubes can be switched without introducing a sample into the switching valve.

Further, the rotor included in the switching valve of the invention is rotationally movable between a position where the pair of tubes are both blocked, a position where only one of the pair of tubes is blocked, and a position where flows in the pair of tubes are both allowed. According to the above-mentioned structure, flows in the pair of tubes can be blocked and allowed by one drive source.

Furthermore, a rotation center axis of the rotor included in the switching valve of the invention may be disposed at a position deviating from a straight line connecting centers of rotation of the respective pair of rollers, and the pair of pressing members may have the pressing areas that are symmetrical with respect to a straight line passing through the center of rotation of the rotor and extending a horizontal direction. According to the above-mentioned structure, the rotor can easily block and allow a flow in each of the pair of tubes disposed in parallel to each other. Moreover, a rotation center axis of the rotor included in the switching valve of the invention may be disposed on a straight line connecting centers of rotation of the respective pair of rollers, and the pair of pressing members may have the pressing areas that are symmetrical with respect to a straight line passing through the center of rotation of the rotor and extending a vertical direction.

Further, a suction-discharge device of the invention includes the switching valve of the invention, a syringe pump to which end portions of each of the pair of tubes is connected, and a pump drive unit that moves a piston part of the syringe pump forward or backward with respect to a cylinder part. The pump drive unit cooperates with the rotor drive unit to allow a sample to flow in the pair of tubes. According to the above-mentioned structure, even though the contamination of a sample occurs, since the contaminated syringe pump and the contaminated tubes are removed from the suction-discharge device and are easily replaced with a new syringe pump and new tubes, contamination can be easily removed. Since the switching valve and the pump drive unit do not come into direct contact with a sample at the time of this replacement, the contamination in the sample is not spread.

Furthermore, a suction-discharge assembly used in the suction-discharge device of the invention is capable of being mounted on the suction-discharge device, and includes the pair of tubes and the syringe pump to which one end of each of the pair of tubes is connected. The suction-discharge assembly is sterilely packed. According to the above-mentioned structure, when the syringe pump and the tubes are installed on the suction-discharge device, work, such as sterilization or washing treatment, does not need to be performed in advance. In addition, since the length of the tube does not need to be adjusted according to the size of a device to be installed, the suction-discharge assembly can be quickly installed in the suction-discharge device. Accordingly, it is possible to prevent contaminant, which floats in the air, from entering the flow passage.

Further, the suction-discharge device of the invention can be used as pump means for supplying a culture medium of a culture medium replacement apparatus, pump means for sucking and discharging a reagent, such as pressure-transmission water or cell suspension of the dispensing apparatus, and a switching valve. By being so used, culture or tests can be accurately performed without possibility that contamination caused by bacteria or the like may occur.

Furthermore, when an automatic culture system includes a culture medium replacement apparatus or a dispensing apparatus on which the suction-discharge device of the invention is mounted, a culture apparatus that receives a vessel, which receives a sample, in a constant-temperature chamber adjusted to a predetermined environment, and a transport mechanism that transports the vessel between the culture medium replacement apparatus and the culture apparatus, the culture of a sample over a long time period can be automatically performed.

Effect of the Invention

According to the switching valve of the invention, since the flow of a sample can be controlled without allowing the sample to flow in the body, dust generated from the body of the valve does not enter the sample. Further, even though a sample is contaminated with bacteria, a space in which a sample flows can be returned to a clean state by the autoclave sterilization or hydrogen peroxide gas sterilization of the tubes in which a sample flows or simple work for discarding contaminated tubes and installing new sterile tubes. Accordingly, since work for washing the inside of an opening/closing valve can be omitted, the burden of a worker can be reduced.

Furthermore, according to the suction-discharge device of the invention, it is possible to accurately supply a sample without allowing the sample to flow in the body. Moreover, even though a sample is contaminated with bacteria, a space in which a sample flows can be returned to a clean state by the autoclave sterilization or hydrogen peroxide gas sterilization of the tubes and the syringe pump in which a sample flows or simple work for discarding contaminated tubes and the contaminated syringe pump and installing new sterile tubes and a new syringe pump. Accordingly, since work for washing the inside of an opening/closing valve and the pump can be omitted, the burden of a worker can be reduced.

Moreover, according to the suction-discharge assembly of the invention, sterilization work to be performed at the time of installation can be omitted. Accordingly, the burden of a worker can be reduced. Further, it is also possible to reduce a possibility that bacteria or dust may remain after washing work.

MODES FOR CARRYING OUT THE INVENTION

Figure 1:
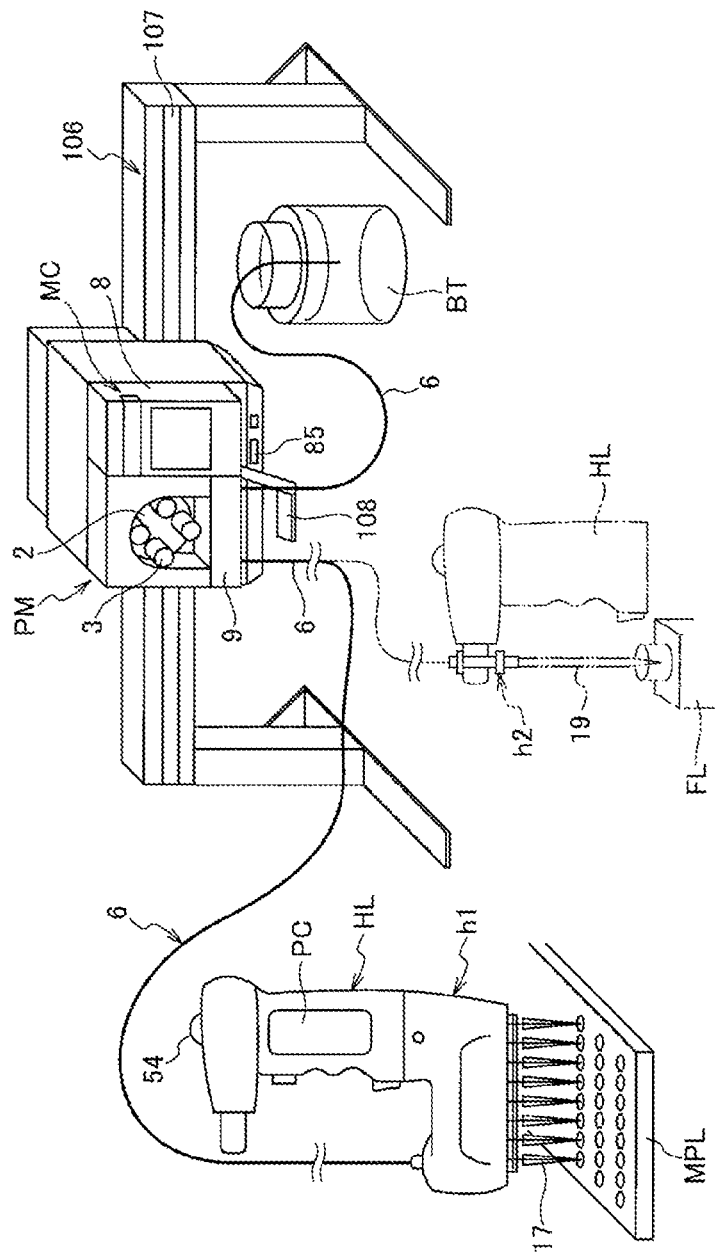
FIG. 1 is a diagram illustrating a suction-discharge device using a tubing pump in the related art.
Figure 2:
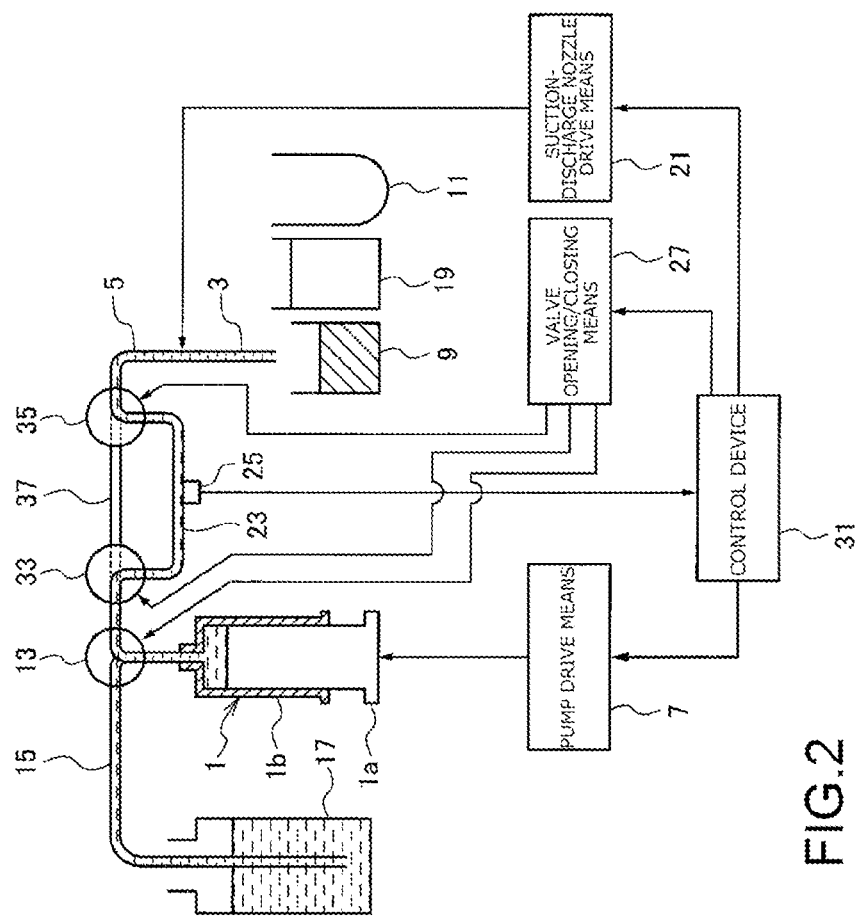
FIG. 2 is a diagram illustrating a suction-discharge device using a switching valve in the related art.
Figure 3:
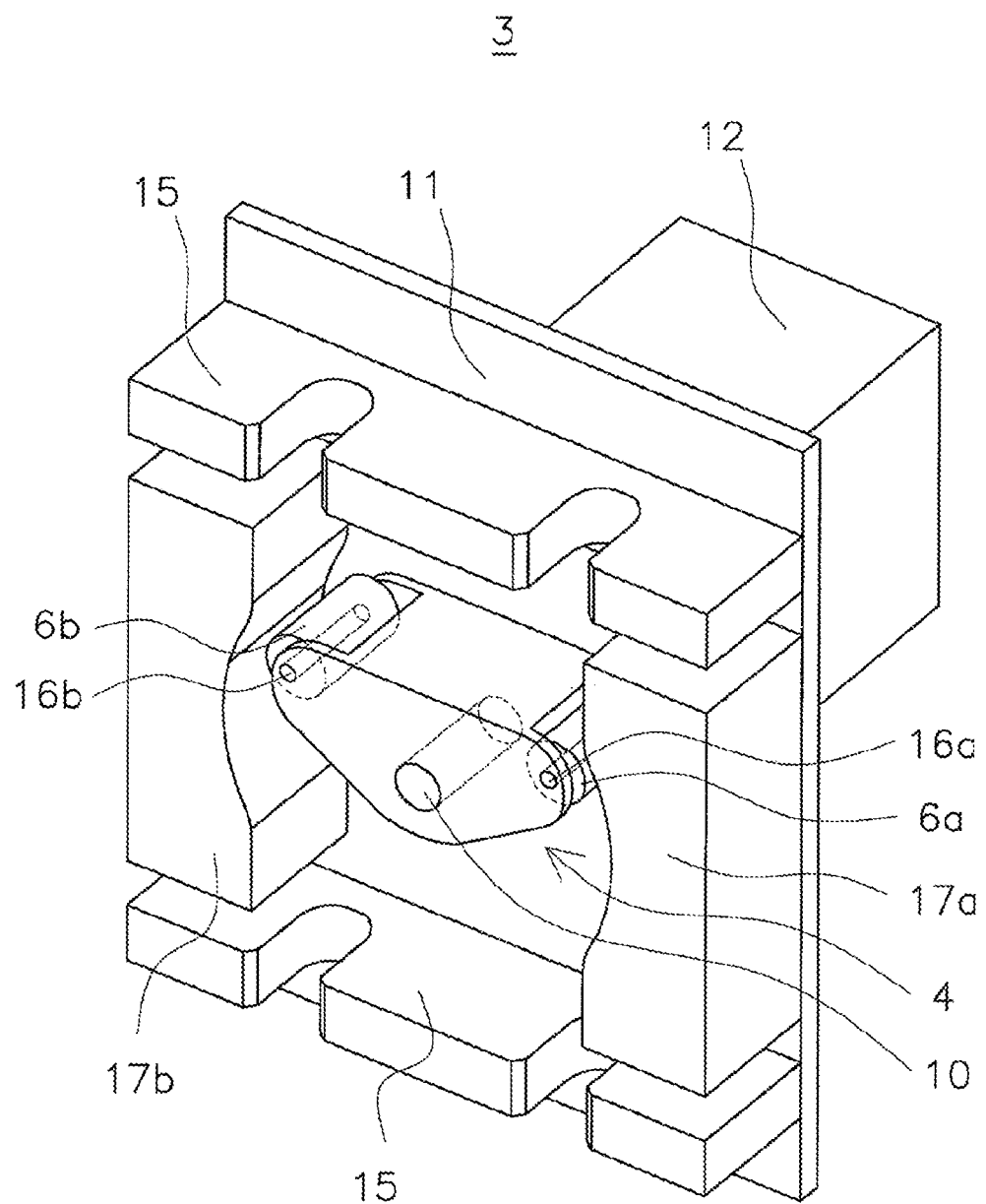
FIG. 3 is a perspective view illustrating an embodiment of a switching valve of the invention.
Figure 4:
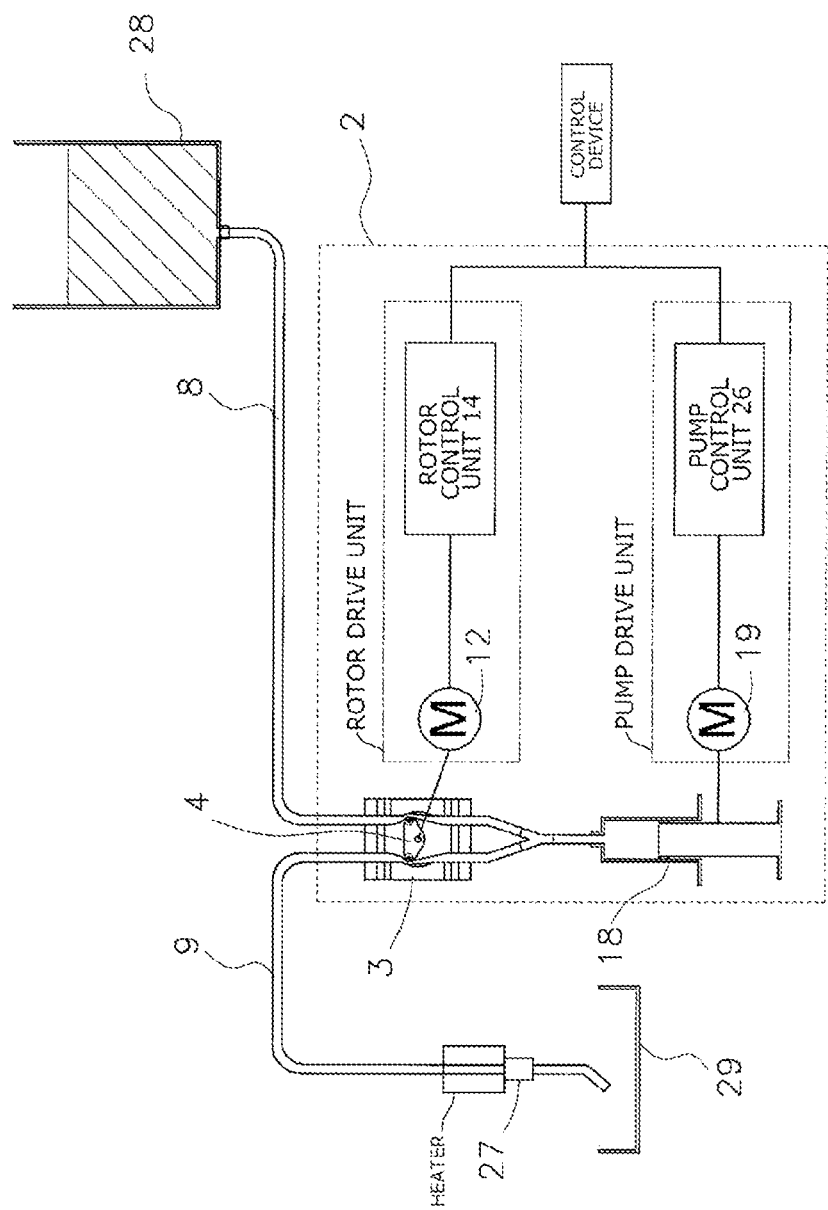
FIG. 4 is a block diagram illustrating the configuration of a suction-discharge device 2 of the invention.
Figure 5:
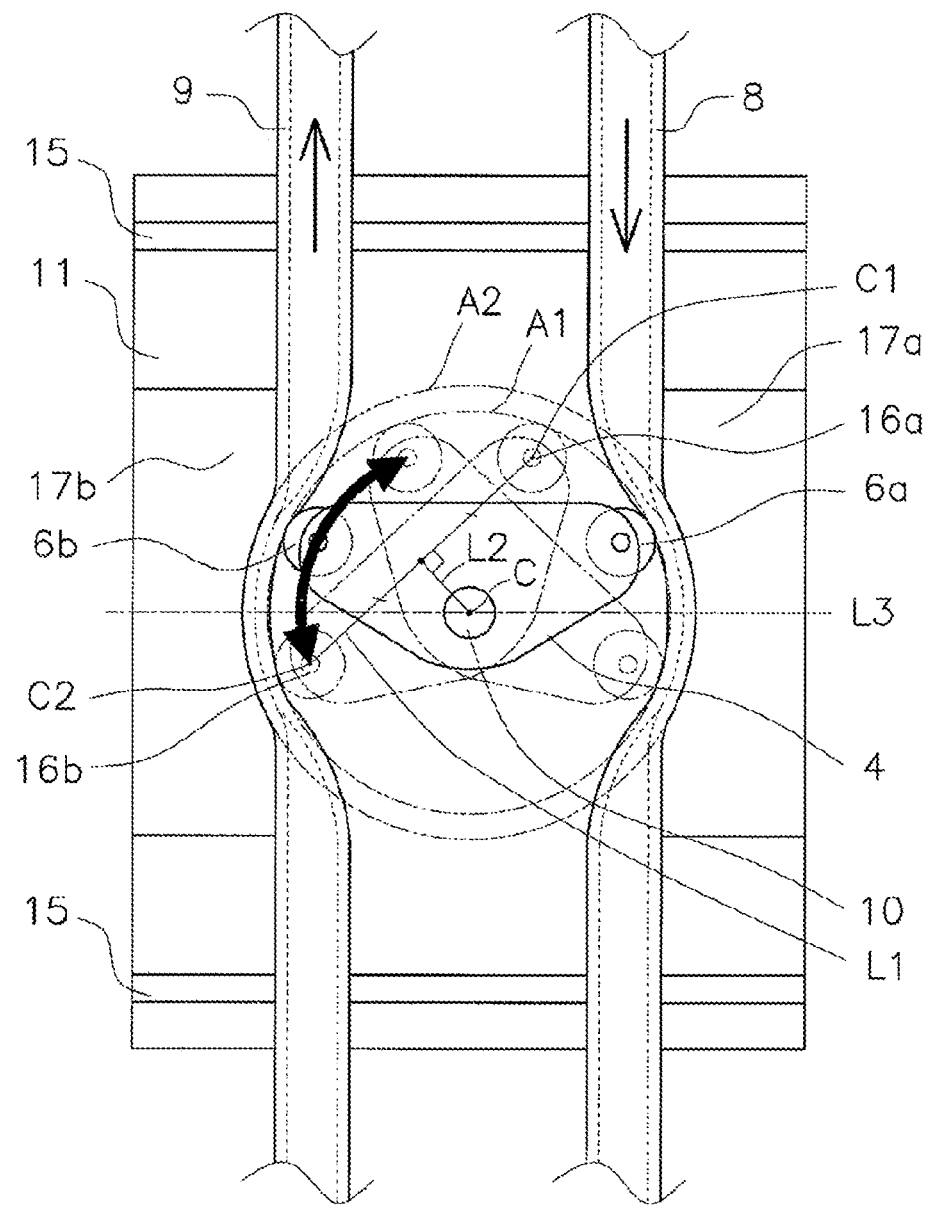
FIG. 5 is a diagram illustrating the operation of a rotor 4 included in the switching valve 3 of the invention.

Embodiments of the invention will be described below with reference to the drawings. FIG. 3 is a perspective view illustrating a switching valve 3 of the invention. FIG. 4 is a block diagram illustrating the configuration of a suction-discharge device 2 of the invention. FIG. 5 is a diagram illustrating the operation of a rotor 4 included in the switching valve 3 of this embodiment. The rotor 4 is disposed at the central portion of the body of the switching valve 3, and rollers 6a and 6b are rotatably mounted on the left and right portions of the rotor 4. Further, tubes 8 and 9 are disposed so as to pass in the vicinity of both side surfaces of the rotor 4. The switching valve 3 is adapted to restrict the flow of a sample in the tube by crushing the tubes 8 and 9 with the rollers 6a and 6b when the rotor 4 is rotated in a predetermined direction. A shaft 10 is fixed to the central portion of the rotor 4. The shaft 10 passes through a base plate 11, and is connected to a motor 12 that is fixed to the surface of the base plate 11 opposite to the surface of the base plate 11 on which the rotor 4 is disposed. A stepping motor of which the rotational direction and the rotation angle can be accurately controlled is used as the motor 12 included in the suction-discharge device 2 of the invention. The operation of the motor 12 is controlled by a rotor control unit 14, and the motor 12 is activated to a predetermined rotational position in a predetermined rotational direction by a signal output from the rotor control unit 14. The motor 12 and the rotor control unit 14 form a rotor drive unit that rotationally operates the rotor 4 to a predetermined angle. Meanwhile, the tubes 8 and 9, which are disposed on the switching valve 3 of this embodiment, are disposed in a vertical direction so as to be parallel to each other in the drawings.

The front shape of the rotor 4 of this embodiment is a substantially triangular shape, and the cylindrical rollers 6a and 6b are rotatably fixed to the rotor 4 at both ends of the body of the rotor 4 through shafts 16a and 16b. The rotor 4 is adapted to be capable of being rotated about the center axis C of the shaft 10 as the center of rotation by the motor 12. Each of the rollers 6a and 6b is moved to revolve on a circular orbit A1, which has a center of rotation on the center axis C of the shaft 10, by the rotational operation of the rotor 4 (see FIG. 5). Pressing members 17a and 17b are disposed at left and right positions, which are symmetrical with each other, outside the revolution orbit A1 of each of the rollers 6a and 6b. The surface (inner surface) of each of the pressing members 17a and 17b facing the rotor 4 is machined in the shape of a curve along a circular arc A2 that has a radius larger than the radius of the revolution orbit A1 of the rollers 6a and 6b. The inner surfaces of the pressing members 17a and 17b, which are formed along the circular arc A2, and the respective rollers 6a and 6b cooperate with each other to press the tubes 8 and 9, respectively, so that flows in the tubes 8 and 9 are blocked. The blocking areas are referred to as pressing areas in this specification. The pressing areas of this embodiment are formed along the circular arc A2, and are formed so as to be symmetrical with respect to a straight line L3 that passes through the center axis C of the shaft 10 and extends in a horizontal direction. Meanwhile, it is preferable that the radius of the circular arc A2 of the pressing area is set to a radius obtained as the sum of the radius of the circular arc A1 serving as the orbit of each of the rollers 6a and 6b and the thickness of each of the pressed tubes 8 and 9. Furthermore, in this embodiment, the pressing areas have a shape that is symmetrical with respect to a straight line passing through the center axis C of the shaft 10 and extending in a vertical direction. Since the pressing areas are provided as described above, the rotor 4 is rotated in a predetermined direction by the activation of the motor 12 and the rollers 6a and 6b are also operated to revolve with the rotation of the rotor 4. Accordingly, the rollers 6a and 6b approach or are separated from the corresponding pressing members 17a and 17b, respectively. The tubes 8 and 9, which are disposed between the rotatably mounted rollers 6a and 6b and the pressing members 17a and 17b, are pinched or opened by the revolution of the rollers. Accordingly, the flows of a sample in the tubes 8 and 9 can be controlled. Meanwhile, it is preferable that members forming the switching valve 3 of the invention are made of stainless steel or a resin having excellent heat resistance and excellent chemical resistance, such as PTFE or a polyimide resin, in consideration of the fact that various kinds of sterilization treatment, such as autoclave sterilization and hydrogen peroxide gas sterilization, are performed.

The rollers 6a and 6b are mounted so as to be rotatable about center axis C1 and C2 of the shafts 16a and 16b as the centers of rotation, respectively. Further, the rotation center axis C of the rotor 4 is disposed at a position that deviates from the middle point of a line L1 connecting the centers of rotation of the respective rollers 6a and 6b. In an example illustrated in FIG. 5, the center of rotation of the rotor 4 is disposed on the perpendicular bisector of a line that connects the centers of rotation of the respective rollers 6a and 6b. Accordingly, when the rotor 4 is rotationally operated to a predetermined rotational position, the flow of a sample in one tube 9 of the tubes 8 and 9 disposed in parallel to each other can be allowed while the flow of a sample in the other tube 8 is restricted. In addition, when the rotor 4 is rotationally moved to another rotational position, the flows of a sample in both the tubes 8 and 9 can be restricted. Further, since a sample passes through the inside of the tubes and does not flow in a valve body as in the switching valve of Patent Document 2, dust generated from the switching valve 3 does not contaminate the sample. Furthermore, the rollers 6a and 6b included in the switching valve 3 of this embodiment are formed in the shape of a cylinder of which the side surface extends along a straight line. However, the shape of each roller is not limited thereto and each roller may be formed in the shape of a barrel, which gradually becomes narrow toward both ends thereof from a cylindrical central portion thereof, as another example. The rollers 6a and 6b cooperate with the pressing members 17a and 17b to press, that is, crush the tubes 8 and 9, so that flows in the tubes 8 and 9 are blocked. For this reason, when an excessive force is repeatedly applied to crease portions of the crushed tubes 8 and 9, plastic deformation is generated at the crease portions and the crease portions deteriorate rapidly. Accordingly, since a pressing force to be applied to the crease portion is reduced when each roller is formed in the shape of a barrel of which the diameter of a portion to come into contact with the crease portion is smaller than the diameter of a central portion, the early deterioration of the tubes 8 and 9 can be prevented.

Figure 6A:
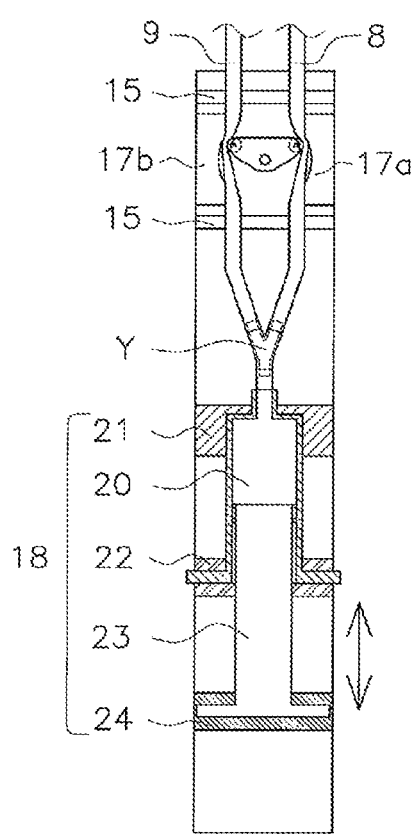
FIGS. 6(a) and 6(b) are a front view and a side view of the suction-discharge device 2 of the invention of which apart are illustrated as a cross-section.
Figure 6B:
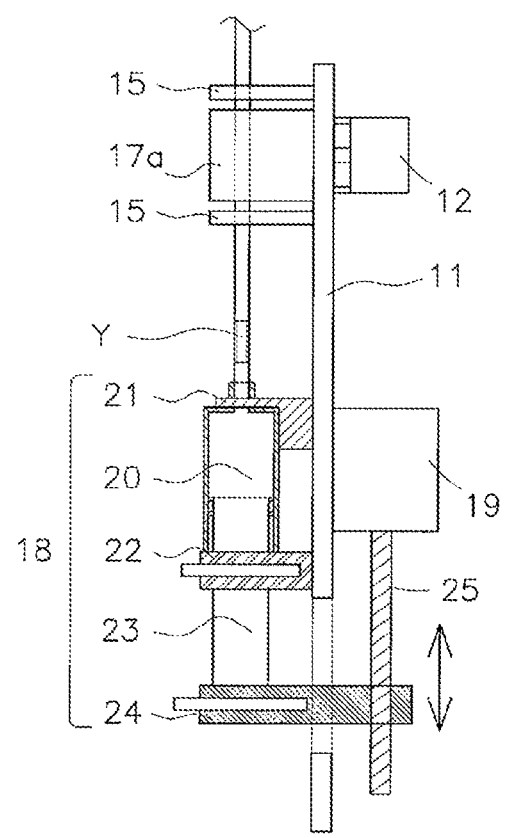

Next, a syringe pump 18 included in the suction-discharge device 2 of the invention will be described. FIG. 6(a) is a diagram of the suction-discharge device 2 of this embodiment viewed from the front, and FIG. 6(b) is a diagram thereof viewed from the side. For easy understanding of illustration, the portions of FIGS. 6(a) and 6(b) corresponding to the syringe pump 18 are illustrated as a cross-section. The suction-discharge device 2 of this embodiment is adapted to drive a syringe type syringe pump 18 by a motor 19. The base plate 11 of the suction-discharge device 2 is provided with brackets 21 and 22 that position and fix a cylinder part 20 at a predetermined position. The base plate 11 is further provided with a piston bracket 24 that is engaged with a piston part 23 and is used to move the piston part 23 forward and backward with respect to the cylinder part 20. The piston bracket 24 is fixed to a mover of a feed screw mechanism 25 that is connected to a rotating shaft of the motor 19 and converts the rotational motion of the motor 19 into a linear motion. Since the piston bracket 24 is moved forward or backward in conjunction with the rotational operation of the motor 19, the piston bracket 24 moves the piston part 23 forward and backward with respect to the cylinder part 20. Meanwhile, a stepping motor of which the rotational direction and the rotation angle can be accurately controlled is used as the motor 19. The operation of the motor 19 is controlled by a pump control unit 26, and the motor 19 is adapted to be activated to a predetermined rotational position in a predetermined rotational direction by a signal output from the pump control unit 26.

The motor 19 and the pump control unit 26 form a pump drive unit that moves the piston part 23 of the syringe pump 18 forward or backward to predetermined positions with respect to the cylinder part 20. A sample can be accurately sucked and discharged by this structure. Further, the rotor drive unit and the pump drive unit can cooperate with each other to accurately suck a sample, which is stored in a tank 28, by a predetermined amount and to discharge the sample from a discharge nozzle 27.

Figure 7A:
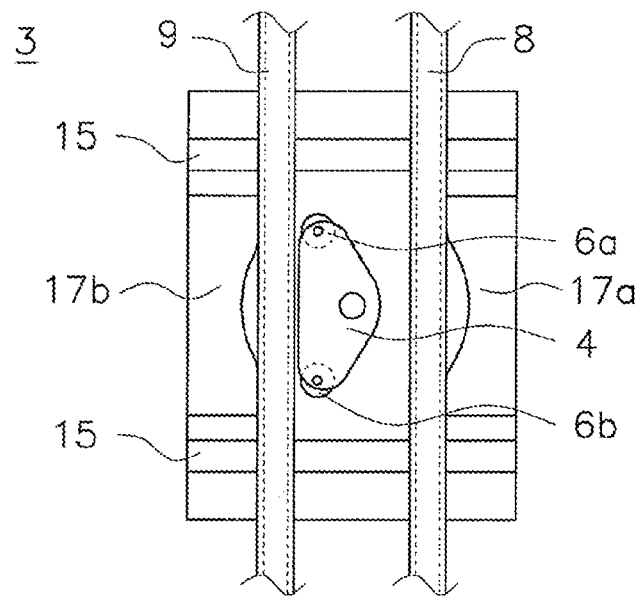
FIGS. 7(a) and 7(b) are diagrams illustrating the operation of the rotor 4 included in the switching valve 3 of the invention.

First, a suction-discharge assembly, which includes the suction-side tube 8, the discharge-side tube 9, and the syringe pump 18, is mounted on the suction-discharge device 2 at a predetermined position to activate the suction-discharge device 2. The respective tubes 8 and 9 are positioned and fixed at predetermined positions between the rotor 4 and the pressing members 17a and 17b in parallel to each other by tube fixing members 15 that are mounted on the switching valve 3. In each tube fixing member 15, grooves having widths smaller than the diameters of the tubes 8 and 9 are formed at a plate-like member. When the tubes 8 and 9 are pushed into the grooves, the tubes 8 and 9 are fixed. Further, since the tubes 8 and 9, which have been pushed, are merely fixed by the repulsive forces of the tubes, the tubes 8 and 9 can be easily removed from the tube fixing members 15 and replaced. The tube fixing members 15 are mounted on the switching valve 3 above and below the rotor 4, respectively. Meanwhile, it is preferable that the rotor 4 of the switching valve 3 is stopped at a position where the rollers 6a and 6b do not press the tubes 8 and 9 when the tubes 8 and 9 are to be replaced. The position where the tubes 8 and 9 are not pressed by the rollers 6a and 6b is referred to as a tube-open position (see FIG. 7(a)). Further, the motor 19 is stopped at a position where the piston part 23 of the syringe pump 18 to be mounted is most pushed into the cylinder part 20, that is, a position where the internal volume of the cylinder part 20 is smallest. Meanwhile, end portions of the tubes 8 and 9, which are disposed adjacent to the rotor 4, are connected to two input/output portions of a Y-shaped tube connector Y, respectively. The Y-shaped tube connector Y includes two input/output portions provided at one end thereof and one input/output portion provided at the other end thereof, and one input/output portion provided at the other end of the Y-shaped tube connector Y is connected to the tip of the syringe pump 18.

Figure 7B:
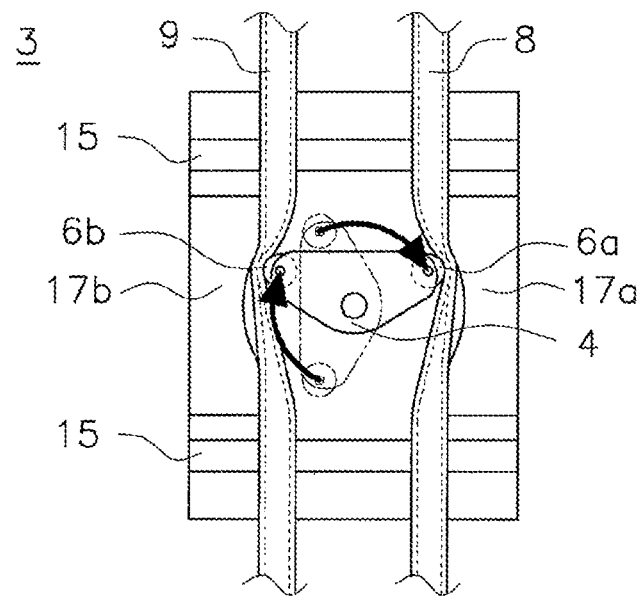

First, the tubes 8 and 9 are mounted on the syringe pump 18. Then, the rotor 4 is rotated to a position where flows in the tubes 8 and 9 are blocked between the pressing members 17a and 17b to which the respective rollers 6a and 6b correspond. A position (see FIG. 7(b)) where flows in the tubes 8 and 9 are blocked by the rollers 6a and 6b to which the respective tubes 8 and 9 correspond is referred to as a tube-blocked position. In a state in which flows in the respective tubes 8 and 9 are blocked, the other end of the suction-side tube 8 is connected to the tank 28 that stores a sample, and the other end of the discharge-side tube 9 is connected to the discharge nozzle 27. The preparation of the suction-discharge device 2 of the invention is completed with this. Meanwhile, the discharge nozzle 27 is a tip member used to discharge a sample, which is supplied from the syringe pump 18, to a predetermined vessel, and the detail of the discharge nozzle 27 will be described later.

Figure 8A:
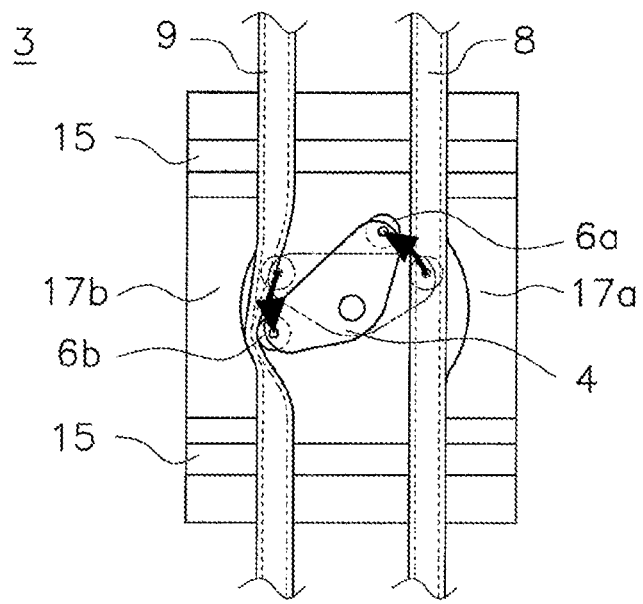
FIGS. 8(a) and 8(b) are diagrams illustrating the operation of the rotor 4 included in the switching valve 3 of the invention.

Next, operations for sucking and discharging a sample, which are performed by the suction-discharge device 2 of this embodiment, will be described. First, the motor 12 is activated to rotate the rotor 4, which has been present at the rotational position where flows in the tubes 8 and 9 are blocked, to a first position (see FIG. 8(a)) where a flow in the suction-side tube 8 is allowed and a flow in the discharge-side tube 9 is blocked. Then, the motor 19 is activated to move the piston part 23 of the syringe pump 18 backward with respect to the cylinder part 20. A sample, which is stored in the tank 28, is sucked into the suction-discharge assembly by the backward movement of the piston part 23. In this case, since the tube 9 is in a state in which a flow is blocked, the air of the external environment is not sucked through the discharge nozzle 27. When the piston part 23 is moved backward to a predetermined position, the motor 19 is stopped.

Figure 8B:
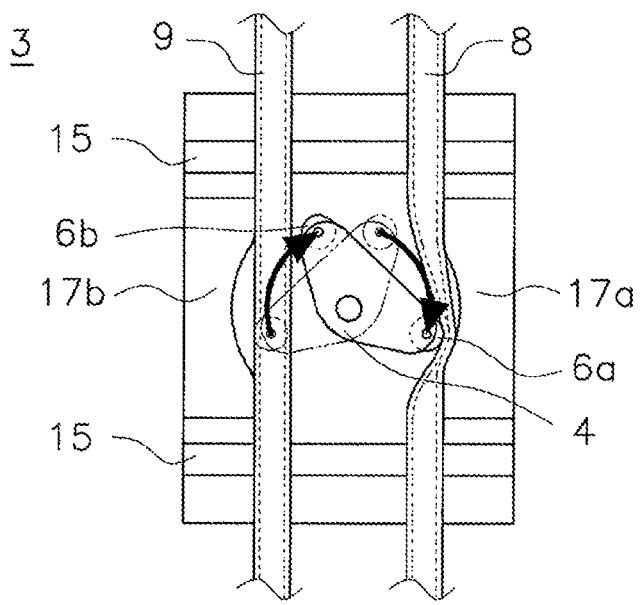

Next, the motor 12 is activated to rotate the rotor 4 to a second position (see FIG. 8(b)) where a flow in the suction-side tube 8 is blocked and a flow in the discharge-side tube 9 is allowed. After that, the motor 19 is activated to move the piston part 23 forward with respect to the cylinder part 20, so that a sample and air sucked into the cylinder part 20 are discharged to the outside through the tube 9 and the discharge nozzle 27. When the discharge operation ends, the motor 12 is driven in a direction opposite to the previous direction to rotate the rotor 4 to a position where the rollers 6a and 6b block flows in the corresponding tubes 8 and 9, respectively. A series of suction/discharge operations, which are performed by the suction-discharge device 2, are completed with this. Meanwhile, when air in the tubes 8 and 9 is not completely discharged in a series of suction/discharge operations, the suction-discharge assembly can be filled with a sample by the repetition of the above-mentioned suction/ discharge operations and an accurate amount of sample can then be discharged from the discharge nozzle 27 by the subsequent suction/discharge operations.

Figure 9A:
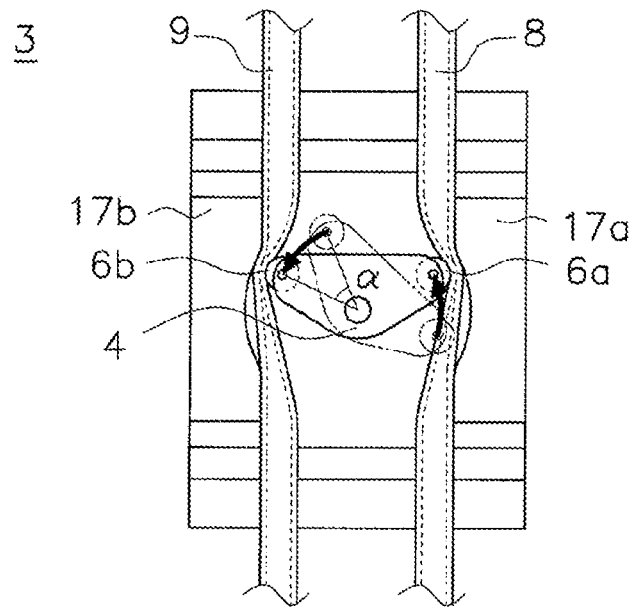
FIGS. 9(a) and 9(b) are diagrams illustrating the operation of the rotor 4 included in the switching valve 3 of the invention.

The switching valve 3 of this embodiment performs an operation for rotating the rotor 4 by a predetermined angle in a predetermined direction to selectively block or open the suction-side tube 8 and the discharge-side tube 9 and control the flows of a sample and gas present in the tubes. That is, when the rotor 4 is rotated, the rollers 6a and 6b cooperate with the corresponding pressing members 17a and 17b to crush the tubes 8 and 9 from the outside. Accordingly, the internal spaces of the tubes 8 and 9 are blocked so that flows in the tubes 8 and 9 are blocked. A blocking operation for the discharge-side tube 9 will be described herewith reference to FIGS. 9(a) and 9(b). The rotor 4, which is drawn in FIG. 9(a) by a two-dot chain line, indicates a position where a flow in the suction-side tube 8 is blocked and a flow in the discharge-side tube 9 is allowed. This position is referred to as the second position. The motor 12 is activated to rotate the rotor 4 from this position in a counterclockwise direction on the plane of paper by an angle α. The discharge-side tube 9 is also pinched between the roller 6b and the pressing member 17b from an open state by this rotational operation, so that the discharge-side tube 9 is in a state in which a flow in the discharge-side tube 9 is blocked (the state of the rotor 4 illustrated in FIG. 9(a) by a solid line). Meanwhile, even while the rotor 4 is rotated by a predetermined angle as described above, the roller 6a and the pressing member 17a are being maintained in a state in which a flow in the suction-side tube 8 is blocked.

Figure 9B:
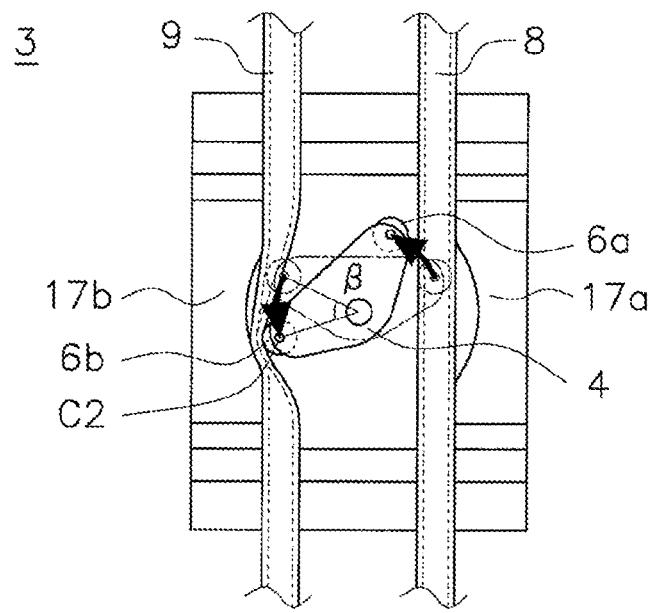

Next, as illustrated in FIG. 9(b) by a solid line, the motor 12 is activated to further rotate the rotor 4 in the counterclockwise direction by an angle β. Due to this operation, the roller 6a deviates from an area in which the roller 6a cooperates with the pressing member 17a to block a flow in the tube 8 and the tube 8 is in a state in which a flow in the tube 8 is allowed. Further, even while the rotor 4 is rotated by the angle β, a state in which the roller 6b presses the discharge-side tube 9 against the pressing member 17b is maintained. That is, the roller 6b is moved in the pressing area while rotating about the center axis C2 of the shaft 16b as the center of rotation. During the operation of the roller 6b, the discharge-side tube 9 is squeezed in a direction opposite to a discharge direction by the roller 6b and the pressing member 17b. Meanwhile, since the roller 6b is moved relative to the tube 9 while being rotated, the tube 9 is not significantly damaged by friction. Since the tube 9 is squeezed in the direction opposite to the flow direction of a sample, it is possible to prevent liquid from dripping from the discharge nozzle 27 after the completion of the discharge of the sample. This is the same action as a publicly known suck-back valve. In this way, the switching valve 3 of the invention can perform the blocking and suck-back of the flow of a sample in the tube by the rotational operation of the rotor 4.

A sample (culture medium) is generated through the adjustment of nutrients or antibiotics that are required for the growth of a cell, medical agents that are used to collect cells and are required for cell desquamation, and the like. A sample, which is to be supplied by a dispensing apparatus or a culture medium replacement apparatus, is preserved under a low-temperature environment for the purpose of prevention of deterioration. Cells are usually grown under an environment of 37° C. Accordingly, when a sample being preserved at a low temperature is supplied at the time of replacement of a culture medium, the cells are significantly damaged due to the low temperature of the sample. For the prevention of the damage of the cells caused by the low temperature of a sample, the sample is supplied while being heated to a predetermined temperature by a heater when the sample is to be supplied. The suction-side tube 8 or the discharge-side tube 9 is provided with a heater, and the discharge nozzle 27 is further provided with a heater. When each of the discharge-side tube 9 and the discharge nozzle 27 is provided with the heater as described above, a sample remaining in the tube is heated by the heater and the volume of the sample is increased. For this reason, even though the discharge of a sample is stopped, surplus liquid droplets fall from the tip of the discharge nozzle 27. The suck-back effect of the switching valve 3 of the invention is useful to prevent a defect such as the fall of surplus liquid droplets.

Next, the suction-discharge assembly, which includes the tubes 8 and 9 and the syringe pump 18 applied to the suction-discharge device 2 of the invention, will be described. Considering the fact that the tubes 8 and 9 are pressed from the outside by the rollers 6a and 6b of the switching valve 3, it is preferable that the tubes 8 and 9 applied to the suction-discharge device 2 of the invention are made of a highly flexible material having a restoring force, such as silicon rubber or polyolefin, fluororubber, or thermoplastic elastomer. Further, a syringe pump made of general glass or a resin can also be used as the syringe pump 18. However, considering the ease of operation or the cost of a disposable syringe pump, it is preferable that the syringe pump 18 may be made of a resin, such as polypropylene or polyethylene. Particularly, the suction-discharge device 2 of the invention has a structure in which the tubes 8 and 9 and the syringe pump 18 are easily replaced. For this reason, all the tubes 8 and 9 and the syringe pump 18 having been used are discarded by simple replacement work after the suction and discharge of a sample, and new tubes and a new syringe pump can be used at the time of the next suction/discharge operations. Accordingly, the contamination of a sample or a specimen can be easily prevented. Meanwhile, if publicly known connecting members, such as luer connectors or one-touch connectors, corresponding to connecting members of the tank 29 and the nozzle 27 to be connected are provided at the tips of the tubes 8 and 9 in advance, an assembly can be replaced in a shorter time. Particularly, it is preferable that a package in which the tubes 8 and 9, the syringe pump 18, and the connecting members integrated and subjected to publicly known sterilization treatment, such as autoclave sterilization or gamma sterilization, are hermetically sealed is prepared as a set of assembly.

Next, a second embodiment of the invention will be described with reference to FIG. 10.

In the switching valve 3 of the first embodiment, the rotation center axis C of the body of the rotor 4 is disposed at a position that is offset from the straight line L1 connecting the center axes C1 and C2 of the shafts 16a and 16b of the rollers 6a and 6b disposed at both ends of the rotor 4 (a position deviating from the straight line L1). In contrast, in a switching valve 3' of the second embodiment of the invention, the center axis C of a shaft 10 of a rotor 4' is disposed on a straight line L1 connecting the center axes C1 and C2 of shafts 16a and 16b. As described above, the first and second embodiments are different from each other in terms of a positional relationship between the rotation center axis C of the rotor and the straight line connecting the rotating shafts C1 and C2 of rollers 6a and 6b. Accordingly, in the second embodiment, the positions of the pressing members also need to be switched so as to correspond to the positions of the respective rotating shafts to perform various opening/closing operations for a position where both tubes 8 and 9 are fully blocked, a position where both the tubes 8 and 9 are fully opened, the first position, and the second position.

Figure 10:
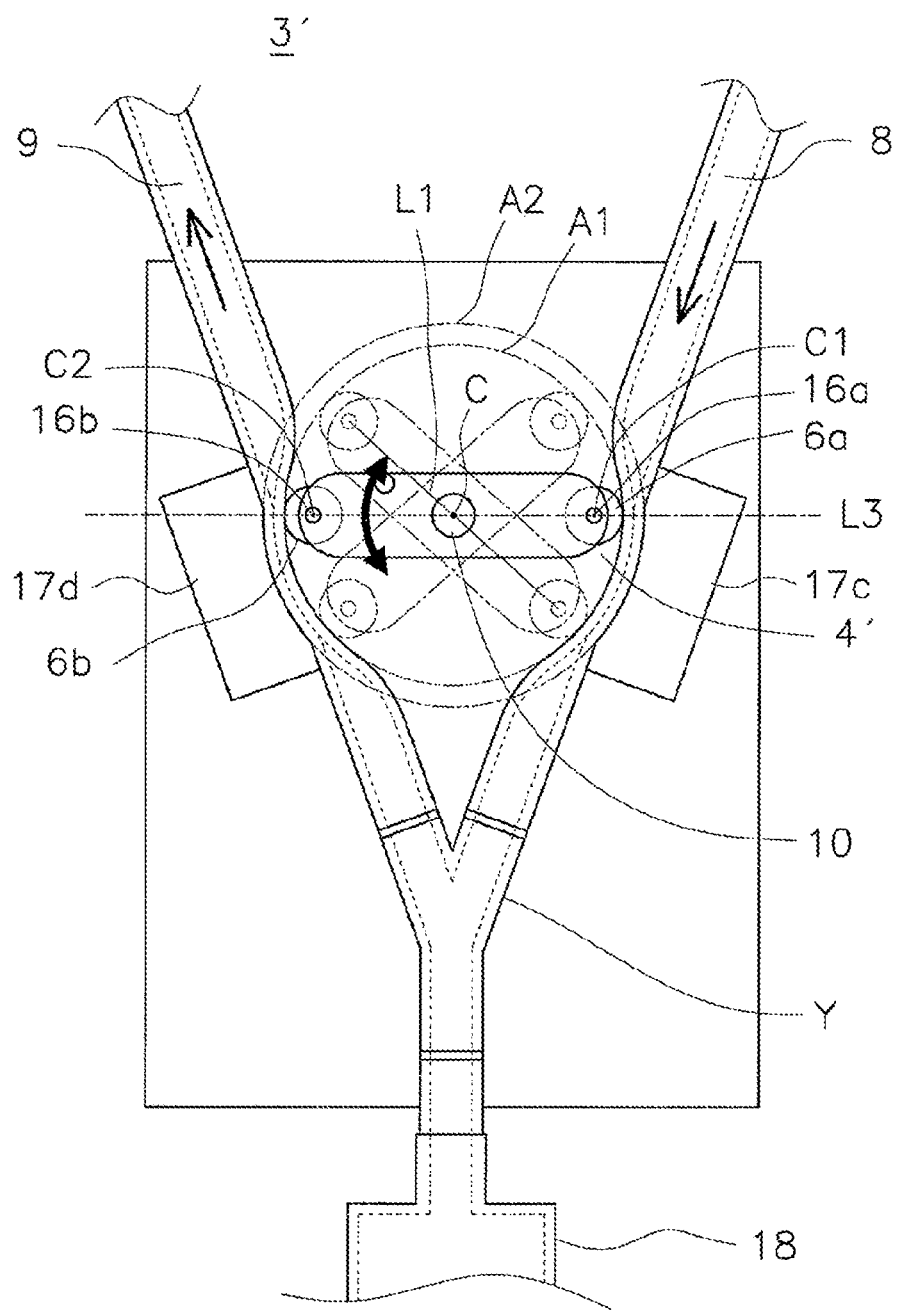
FIG. 10 is a diagram illustrating a switching valve 3' that is a second embodiment of the invention.

FIG. 10 is a diagram illustrating the outline of the switching valve 3', which is a second embodiment of the invention, from the front. Even in the case of the rotor 4' of this embodiment, as in the first embodiment, substantially cylindrical rollers 6a and 6b are rotatably fixed to a body of the rotor at both ends of the body of the rotor through the shafts 16a and 16b. The rotor 4' is adapted to be capable of being rotated about the center axis C of the shaft 10 as the center of rotation by a motor 12. Each of the rollers 6a and 6b is moved to revolve on a circular orbit A1, which has a center on the center axis C of the shaft 10, by the rotational operation of the rotor 4. Pressing members 17c and 17d are disposed on left and right sides outside the revolution orbit A1 of each of the rollers 6a and 6b so as to be symmetrical with each other. The surface of each of the pressing members 17c and 17d facing the rotor 4' is machined in a shape along a circular arc A2 that has a radius larger than the radius of the revolution orbit A1 of the rollers 6a and 6b. According to the above-mentioned structure, the rotor 4' is rotated in a predetermined direction by the activation of the motor 12 and the rollers 6a and 6b are also moved to revolve with the rotation of the rotor 4'. Accordingly, the rollers 6a and 6b approach or are separated from the corresponding pressing members 17c and 17d, respectively. Since the tube 8 disposed between the roller 6a and the corresponding pressing member 17c and the tube 9 disposed between the roller 6b and the corresponding pressing member 17d are pinched to be blocked or are opened by the approach or separation of the rollers 6a and 6b, flows in the tubes 8 and 9 can be controlled.

In the first embodiment, the rotation center axis C of the rotor 4 is disposed at a position that deviates from the straight line connecting the rotation center axes C1 and C2 of the respective rollers 6a and 6b, and the pressing areas where the tubes 8 and 9 are pressed have a shape that is symmetrical with respect to the straight line L3 that passes through the rotation center axis C and extends in the horizontal direction. In contrast, in the second embodiment, the rotation center axis C of the rotor 4 is disposed on the straight line connecting the rotation center axes of the respective rollers 16a and 16b. For this reason, the pressing areas where the tubes 8 and 9 are pressed are not present at positions that are symmetrical with respect to the straight line L3 passing through the rotation center axis C and extending in the horizontal direction. The respective pressing members 17c and 17d are disposed to be capable of being positioned at positions where both the tubes 8 and 9 are simultaneously blocked or opened or only one of the tubes 8 and 9 is blocked when the pressing areas corresponding to the respective rollers 6a and 6b are moved to be rotated about the center axis C as the center of rotation by a predetermined angle.

Further, the tubes 8 and 9 of the first embodiment are disposed in the vertical direction so as to be parallel to each other, but the tubes 8 and 9 of this embodiment are disposed with a predetermined angle therebetween so as to be symmetrical with respect to a straight line extending in the vertical direction. Accordingly, when the rotor 4' is present at a first position where only the discharge-side tube 9 is blocked or a second position where only the suction-side tube is blocked, the open state of the tube to be opened can be made sure. The tubes 8 and 9, which are disposed with a predetermined angle therebetween, are connected to a tube connector Y. The other end of the tube connector Y is connected to a syringe pump 18 below the switching valve 3'.

As in the first embodiment, the rotor 4', which is included in the switching valve 3' of this embodiment, is adapted to be capable of being rotated about the center axis C as the center of rotation by the motor 12 and a rotor control unit 14. Further, the rotor 4' is adapted to be capable of being rotationally moved to a rotational position that is stored in the rotor control unit 14 in advance. According to the above-mentioned structure, the rotor drive unit can cooperate with a pump drive unit, which drives the syringe pump 18, to suck a sample, which is stored in a tank 28, and to discharge the sample from a discharge nozzle 27.

Figure 11:
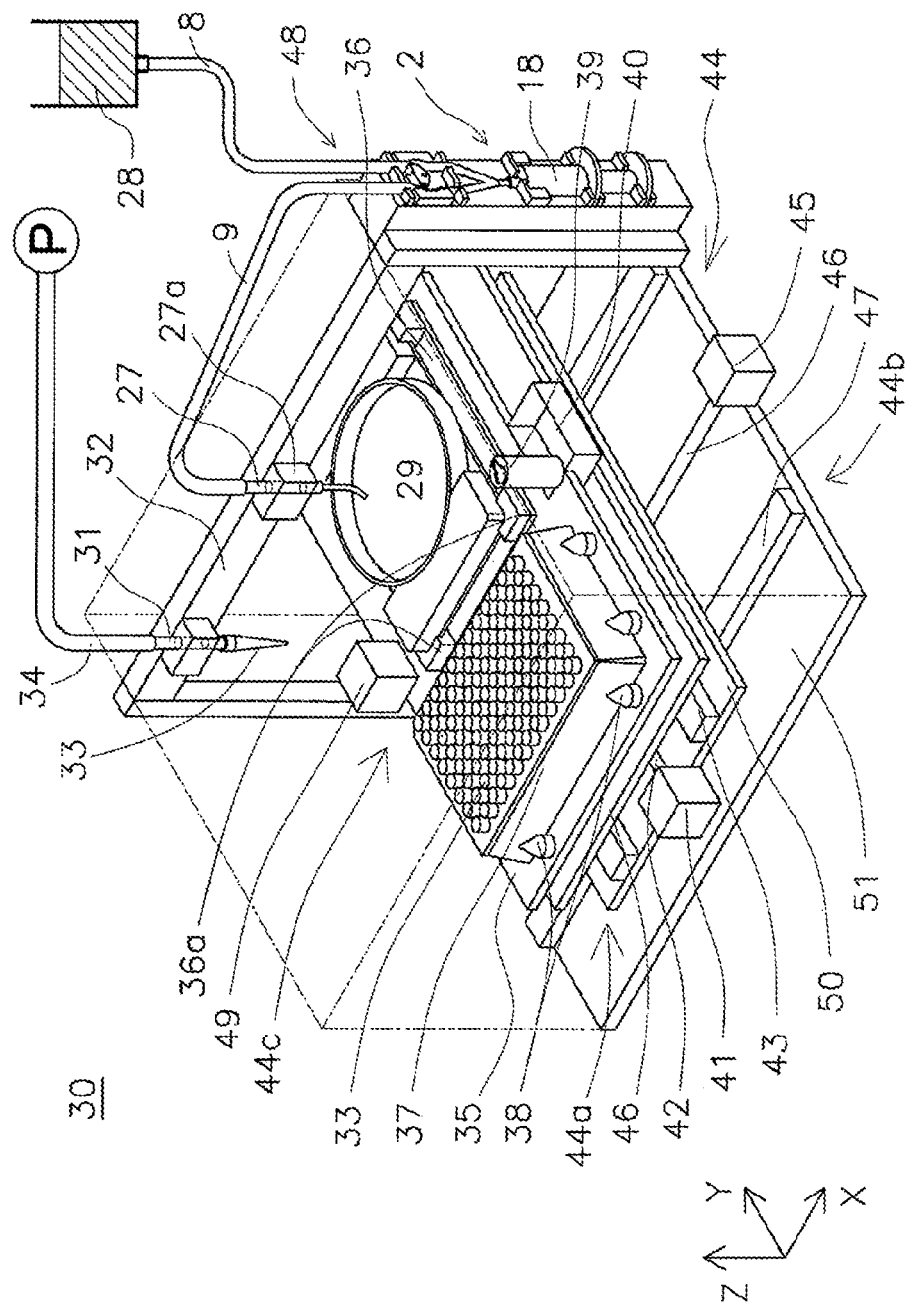
FIG. 11 is a perspective view illustrating an embodiment of a culture medium replacement apparatus of the invention.

Next, a culture medium replacement apparatus 30, which uses the suction-discharge device 2 of the invention, will be described. FIG. 11 is a perspective view illustrating the outline of the culture medium replacement apparatus 30 of the invention. The culture medium replacement apparatus 30 of this embodiment is an apparatus for replacing a solution, which is referred to as a culture medium including water and nutrients, for microorganisms or cells, which are cultured in a vessel 29, at predetermined intervals. First, operations for replacing a culture medium is performed by sucking an old culture medium present in the vessel 29 to remove the old culture medium and then adding a new culture medium. In the culture medium replacement apparatus 30 of this embodiment, the removal of an old culture medium is performed by a suction nozzle 31 and the supply of a new culture medium is performed by the discharge nozzle 27 connected to the suction-discharge device 2 of the invention.

The discharge nozzle 27, which is included in the culture medium replacement apparatus 30 of the invention, is fixed to a beam member 32 that is installed so as to stride over the upper portion of a body of the culture medium replacement apparatus 30. One end of the discharge-side tube 9 is connected to the base end portion of the discharge nozzle 27. The other end portion of the discharge-side tube 9 is connected to the syringe pump 18 of the suction-discharge device 2.

Further, a portion of the discharge nozzle 27, which is positioned below a portion of the discharge nozzle 27 fixed to the beam member 32, has the shape of an elongated cylinder and a tip portion thereof is bent at a predetermined angle. When a culture medium is discharged in a state in which the bent tip portion is close to the inner wall of the vessel 29, the culture medium is accumulated on the bottom of the vessel 29 along the inner wall of the vessel 29. Accordingly, a culture medium can be supplied to the vessel 29 without the generation of bubbles. Further, cells, which are attached to the bottom of the vessel 29, are not separated from the bottom by the force of a culture medium to be supplied.

Figure 12A:
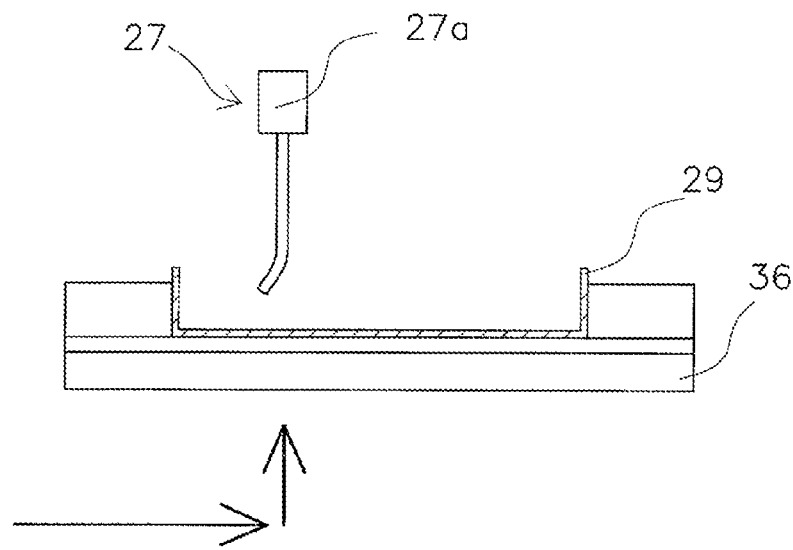
FIGS. 12(a) and 12(b) are diagrams illustrating an operation for supplying a culture medium by the culture medium replacement apparatus of the invention.
Figure 12B:
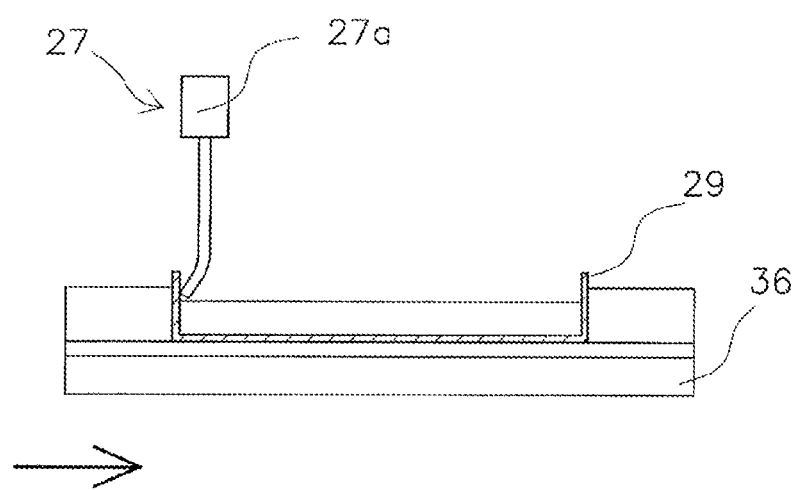

To supply a culture medium to the vessel 29 through the discharge nozzle 27, first, the vessel 29 is moved to a predetermined position, at which the tip portion of the discharge nozzle 27 is positioned below the upper end of the side wall of the vessel 29, by a stage transfer unit 44 (see FIG. 12(a)). Then, the stage transfer unit 44 is further activated to horizontally move the vessel 29 to a position at which the side wall of the vessel 29 and the tip portion of the discharge nozzle 27 are in contact with each other. When the movement of the vessel 29 is completed, a culture medium is discharged from the discharge nozzle 27 (see FIG. 12(b)). The discharged culture medium flows down along the side wall of the vessel 29 and is gradually supplied from the bottom of the vessel 29.

Further, the discharge nozzle 27 is provided with a heater for heating a culture medium, which is preserved at a low temperature, to a temperature at which microorganisms or cells as an object to be cultured are not damaged. The heater of this embodiment is a cartridge heater in which a heating element is built. The heater is detachably inserted into a heating block 27a in which a flow passage for a culture medium is formed. The temperature of the heater is controlled by a temperature control unit (not illustrated), and a culture medium can be supplied after being heated up to a temperature optimal for the culture of a culture medium to be discharged. Meanwhile, the discharge nozzle 27 is detachably fixed by screwing or the like so that the discharge nozzle 27 can be easily attached to and detached from the beam member 32.

The suction nozzle 31, which is included in the culture medium replacement apparatus 30 of this embodiment, is fixed to the beam member 32, and the tip portion of a culture medium-discharge tube 34, which is to be connected to a publicly known suction pump P, is connected to the base end portion of the suction nozzle 31. Further, the tip portion of the suction nozzle 31 is formed in a shape that allows a disposable pipette tip 33 to be attached and detached. The pipette tip 33 is a tip made of an elastic resin, and is inserted into the tip portion of the suction nozzle 31. The pipette tip 33 is fixed by being tightened from the outside with an elastic force. Meanwhile, since a predetermined time has passed after the supply of a culture medium to be sucked by the suction nozzle 31, there is a possibility that the culture medium not only may deteriorate over time but also may be contaminated with bacteria and dust floating in the air. When the pipette tip 33, which has sucked the contaminated culture medium, sucks a culture medium present in other vessels 29, so-called cross-contamination where a contaminant is spread to other vessels 29 by the pipette tip 33 occurs. For the prevention of cross-contamination between the vessels 29, the pipette tip 33 is replaced in the suction nozzle 31 included in the culture medium replacement apparatus 30 of this embodiment whenever the suction of an old culture medium is performed.

Meanwhile, the discharge nozzle 27 can also be adapted so that the pipette tip 33 can be replaced. When the tip of the discharge nozzle has the shape of a straight line as in the case of the suction nozzle 31, elements similar to the pipette tip rack 37 and the tip remover 39 can also be used for the discharge nozzle. In a case in which the tip of the discharge nozzle 27 is bent as in this embodiment, a special pipette tip rack and a special tip remover corresponding to the shape of the tip need to be provided.

The vessel 29 in which a culture medium is to be replaced is positioned and placed on a vessel stage 36, which is disposed on a replacement stage 35, at a predetermined position by positioning members 36a. In addition to the vessel 29, a tip rack 37 is placed at a predetermined position on the replacement stage 35 by positioning members 38. The tip rack 37 receives a plurality of pipette tips 33 in a posture standing in a vertical direction so that the plurality of pipette tips 33 can be mounted on the nozzles 27 and 31. In addition, a tip remover 39 that removes the pipette tip 33 mounted on the discharge nozzle 27 or the suction nozzle 31 and a tip box 40 that stores the removed pipette tip 33 is mounted on the replacement stage 35. The replacement stage 35 can be moved in an X-axis direction, a Y-axis direction, and a Z-axis direction by the stage transfer unit 44.

The replacement stage 35 is disposed on a movable stage 46 that is included in a Y-axis drive mechanism 44a. The Y-axis drive mechanism 44a includes a motor 41, a feed screw mechanism 42 that is connected to the motor 41, and a pair of slide rails 43 that guides the movable stage in the Y-axis direction. The Y-axis drive mechanism 44a moves the movable stage 46 and the replacement stage 35 disposed on the movable stage 46 in the Y-axis direction by the activation of the motor 41. Further, the Y-axis drive mechanism 44a is disposed on an X-axis stage 50. The X-axis stage 50 is moved in the X-axis direction by an X-axis drive mechanism 44b that includes a motor 45, a feed screw mechanism 46 connected to the motor 45, and a pair of slide rails 47 guiding the X-axis stage 50 in the X-axis direction. Further, the X-axis drive mechanism 44b is disposed on a base 51. Furthermore, the replacement stage 35 can be moved relative to the movable stage 46 in the Z direction, that is, a vertical direction by a Z-axis drive mechanism 44c that includes a motor 49, a feed screw mechanism (not illustrated), and a guide mechanism.

Since a stepping motor of which the angle of a rotating shaft can be controlled is used as each of the motors 41, 45, and 49 included in the culture medium replacement apparatus 30 of this embodiment, each of the motors 41, 45, and 49 can be accurately activated to a predetermined position that is instructed in advance. Further, the activation of these motors 41, 45, and 49 and the suction-discharge device 2 is controlled by signals transmitted from a culture medium-replacement control unit (not illustrated, the same shall apply hereinafter). According to the above-mentioned structure, the vessel 29 placed on the replacement stage 35, all pipette tips 33 received in the tip rack 37, the tip remover 39, and the like can be moved relative to the suction nozzle 31 and the discharge nozzle 27 in the X direction, the Y direction, and the Z direction. The mounting of the pipette tip 33 on the suction nozzle 31, the removal (detachment) of the pipette tip 33 mounted on the suction nozzle 31, and the movement of the pipette tip 33 relative to the vessel 29 can be performed by the movement in the respective directions. Furthermore, in a case in which the delivery position of the vessel 29 is set in advance, the delivery of the vessel 29 and the tip rack 37, which are to be transported by a publicly known automatic transport device, can be performed.

Figure 13A:
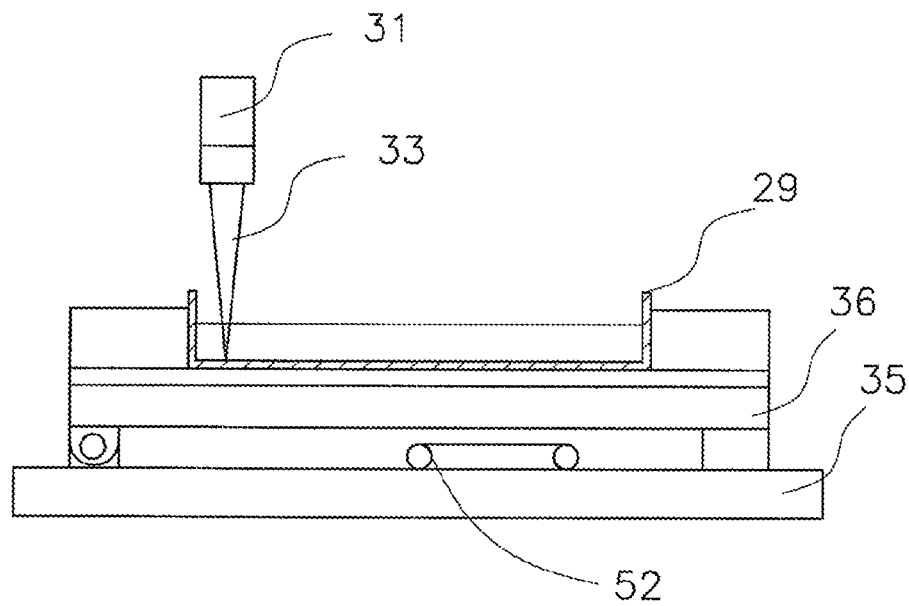
FIGS. 13(a) and 13(b) are diagrams illustrating the operation of a tilt mechanism included in the culture medium replacement apparatus of the invention.
Figure 13B:
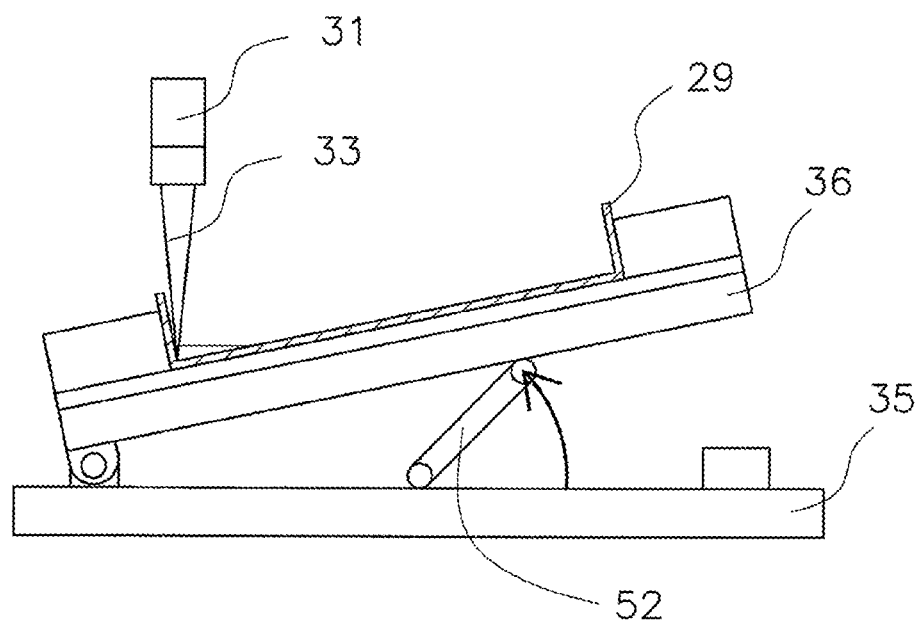

In addition to the above-mentioned structure, as illustrated in FIGS. 13(a) and 13(b), the culture medium replacement apparatus 30 of this embodiment is provided with a tilt mechanism 52, which tilts the vessel stage 36 on which the vessel 29 is placed, to increase the efficiency of the removal of an old culture medium. The tilt mechanism 52 is a mechanism that includes a publicly known drive source, such as a motor or a cylinder, and a mechanism and tilts the vessel stage 36 on which the vessel 29 is placed by a predetermined angle. When the vessel stage 36 is tilted, the rest of a culture medium, which remains after the culture medium is sucked by the suction nozzle 31, can be collected at one point.

A method of sucking a culture medium with the tilt mechanism 52 is as follows. First, when a large amount of culture medium to be discarded remains in the vessel 29, the vessel stage 36 is maintained in a horizontal state as illustrated in FIG. 13(a). Next, when a small amount of culture medium to be discarded remains, the tilt mechanism 52 is activated to tilt the vessel stage 36 by a predetermined angle. Further, the vessel stage 36 is tilted, and the stage transfer unit 44 is activated to move the vessel stage 36 so that the tip of the pipette tip 33 mounted on the suction nozzle 31 has contact with the lowest position of the vessel 29 (see FIG. 13(b)). Accordingly, all of an old culture medium can be removed from the vessel 29.

Next, the procedure of operations for replacing a culture medium, which is performed by the culture medium replacement apparatus 30 of this embodiment, will be described. First, the culture medium-replacement control unit activates the culture medium replacement apparatus 30 and the respective motors 41, 45, and 49 of the stage transfer unit 44 to move the replacement stage 35 to a predetermined position where the replacement stage 35 can receive a vessel 29. When a vessel 29 in which a culture medium needs to be replaced is placed on the vessel stage 36, the culture medium replacement apparatus 30 drives the respective motors 41, 45, and 49 to move the vessel 29 to a position where the suction nozzle 31 can suck a culture medium. When the vessel 29 is moved to a position where the tip of the suction nozzle 31 is inserted into the culture medium, an old culture medium present in the vessel 29 is sucked through the pipette tip 33 and the suction nozzle 31 by the suction force of the publicly known pump P and the culture medium-replacement control unit sucks the old culture medium to be discharged to remove the old culture medium while tilting the vessel 29 by the above-mentioned procedure.

When the removal of the old culture medium ends, the culture medium-replacement control unit activates the tilt mechanism 52 to return the vessel 29 to a horizontal posture from a tilted posture. After that, the culture medium-replacement control unit activates the respective motors 41, 45, and 49 to move the vessel 29 to a position where the discharge nozzle 27 can discharge a culture medium into the vessel 29. When the movement of the vessel 29 is completed, the culture medium-replacement control unit activates the suction-discharge device 2 to supply a culture medium, which is stored in the tank 28, to the vessel 29 by a predetermined amount. Then, when the supply of the culture medium is completed, the culture medium-replacement control unit moves the replacement stage 35 to the delivery position of the vessel 29 that is to be delivered to the transport device. A series of operations for replacing a culture medium are completed with this.

Next, an operation for replacing the pipette tip 33, which is mounted on the suction nozzle 31, will be described. A plurality of pipette tips 33 are stored in the tip rack 37 in a standing posture where the pipette tip 33 can be mounted on the tip portion of the suction nozzle 31. Meanwhile, the tip rack 37 generally receives a predetermined number of pipette tips 33 in a predetermined array so as to correspond to the arrangement of the respective culture compartments (wells) of a microplate of 96-well, 384-well, or 1536-well that is a publicly known culture vessel. In the culture medium replacement apparatus 30 of this embodiment, for easy illustration, the tip rack 37 has a form corresponding to 96-well. As illustrated in FIG. 11, in the tip rack 33 placed on the culture medium replacement apparatus 30 of this embodiment, eight rows, each of which stores twelve pipette tips 33 arranged at predetermined intervals in the X-axis direction, are arranged at predetermined intervals in the Y-axis direction. When the tip rack 37 is installed manually or installed using a publicly known transport device at a predetermined position on the replacement stage 35, the culture medium-replacement control unit activates the stage transfer unit 44 to move the replacement stage 35 so that a target pipette tip 33 is positioned immediately below the suction nozzle 31. After that, the culture medium-replacement control unit activates the Z-axis drive mechanism 44c to raise the replacement stage 35 and the tip rack 37 to a predetermined height. The culture medium-replacement control unit stops the activation of the motor 49 at a position where the pipette tip 33 is mounted on the tip mounting portion of the suction nozzle 31. Then, the culture medium-replacement control unit activates the motor 49 in a reverse rotational direction to lower the replacement stage 35 to a position where the replacement stage 35 is positioned before the replacement stage 35 is raised. Accordingly, the pipette tip 33 having been stored in the tip rack 37 is mounted on the suction nozzle 31.

Next, an operation for removing the mounted pipette tip 33 from the suction nozzle 31 will be described. The tip remover 39 provided on the replacement stage 35 is used to remove the pipette tip 33 from the suction nozzle 31. The tip remover 39, which is included in the culture medium replacement apparatus 30 of this embodiment, includes a punch hole that is formed at the upper cover portion of a hollow cylindrical member and has a shape where a circular hole having a diameter larger than the diameter of the pipette tip 33 is connected to an elongated hole having a diameter larger than the diameter of the tip mounting portion of the suction nozzle 31 and smaller than the diameter of the pipette tip 33.

After the suction of a culture medium ends, the culture medium-replacement control unit activates the stage transfer unit 44 to moves a large circular hole portion of the tip remover 39 to a position immediately below the discharge nozzle 27. Next, the culture medium-replacement control unit activates the Z-axis drive mechanism 44c to raise the tip remover 39 and to insert the target pipette tip 33 into the tip remover 39. Then, the culture medium-replacement control unit moves the tip remover 39 in the horizontal direction to move the tip mounting portion of the suction nozzle 31 to an elongated hole portion of a plate member. Here, the culture medium-replacement control unit activates the Z-axis drive mechanism 44c to lower the tip remover 39, to engage the pipette tip 33 with the elongated hole portion, and to remove the pipette tip 33 from the suction nozzle 31. The removed pipette tip 33 is received in the tip box 40 that is provided below the tip remover 39. When the removal of the pipette tip 33 ends, the culture medium-replacement control unit activates the stage transfer unit 44 to move the tip rack 37 toward the suction nozzle 31 for the mounting of a new pipette tip 33 on the tip portion of the suction nozzle 31. In this way, the culture medium replacement apparatus 30 of this embodiment can automatically perform the suction/discharge of a sample and the replacement of a disposable pipette tip 33. Meanwhile, as described above, the discharge nozzle 29 can also be formed in a shape where the pipette tip 33 can be mounted on the discharge nozzle 29.

Further, it is preferable that the material of the discharge nozzle 27 included in the culture medium replacement apparatus 30 of this embodiment is metal having high thermal conductivity. Particularly, when the discharge nozzle 27 is made of stainless steel that can stand up to autoclave sterilization or hydrogen peroxide gas sterilization, the discharge nozzle 27 can be repeatedly used even after sterilization treatment. Further, the suction nozzle 31 is screwed so that the suction nozzle 31 can be easily attached to and detached from the beam member 32. Furthermore, since the mounting and detachment of the pipette tip 33 are repeatedly performed, it is preferable that the material of the suction nozzle 31 is metal harder than the pipette tip 33. Particularly, when the suction nozzle 31 is made of stainless steel that can stand up to autoclave sterilization or hydrogen peroxide gas sterilization, the suction nozzle 31 can be repeatedly used even after sterilization treatment. Further, when the sterilization treatment of the suction nozzle 31 is performed, it is preferable that the culture medium-discharge tube 34 connected to the suction nozzle 31 is subjected to sterilization treatment together with the suction nozzle 31 or is discarded and replaced with a new tube 34. Furthermore, when the suction-discharge device 2 of the invention and a suction-discharge assembly 48 are used instead of the publicly known pump that sucks an old culture medium, it is possible to easily remove a contaminated portion by discarding a contaminated assembly and mounting a new assembly even though contamination is generated.

Figure 14:
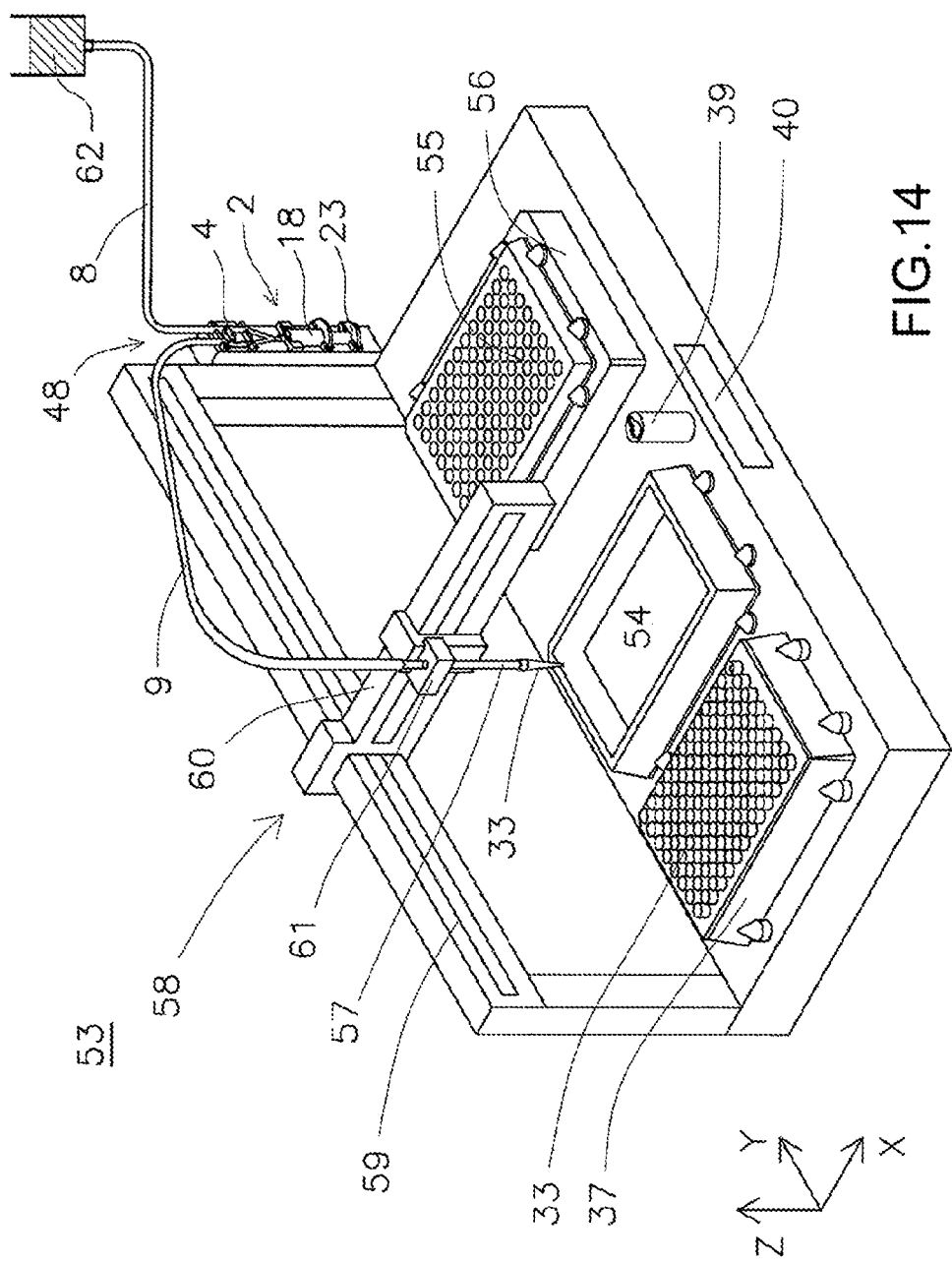
FIG. 14 is a perspective view illustrating an embodiment of a dispensing apparatus of the invention.

In the above description, the culture medium replacement apparatus 30 has been described as one embodiment of an apparatus using the suction-discharge device 2 of the invention. However, other than the culture medium replacement apparatus 30, the suction-discharge device 2 of the invention can also be used for a dispensing apparatus 53 that is used for various tests, such as the biochemical reaction test of a material, in a drug discovery screening field, a biotechnology field, and the like. FIG. 14 is a perspective view illustrating a dispensing apparatus 53 that is another embodiment including the suction-discharge device 2 of the invention.

The dispensing apparatus 53 of this embodiment includes a tip rack 37 that stores a plurality of disposable pipette tips 33, a sample vessel 54, a dispensing stage 56, a dispensing nozzle 57, a nozzle transfer unit 58, a tip remover 39, and a tip box 40 that is disposed below the tip remover 39 and receives a pipette tip 33 removed by the tip remover 39 and waste liquid. A sample, which is used for a test, is stored in the sample vessel 54. A reaction vessel 55 in which a plurality of reaction wells are formed is placed at a predetermined position on the dispensing stage 56 by positioning members. The dispensing nozzle 57 sucks a sample from the sample vessel 54 and discharges the sample to a predetermined reaction well of the reaction vessel 55. The nozzle transfer unit 58 moves the dispensing nozzle 57 in an X direction, a Y direction, and a Z direction. The tip remover 39 is used to remove a pipette tip 33 that has dispensed a sample.

The suction-discharge device 2 included in the dispensing apparatus 53 is connected to the dispensing nozzle 57 through a tube 9, and sucks a sample, which is present in the sample vessel 54, and discharges the sample to each well of the reaction vessel 55 by the reciprocation of the syringe pump 18. The nozzle transfer unit 58 includes a Y-axis drive mechanism 59 that horizontally transfers the dispensing nozzle 57 in the Y-axis direction, an X-axis drive mechanism 60 that is supported by the Y-axis drive mechanism 59 and horizontally transfers the dispensing nozzle 57 in the X-axis direction, and a Z-axis drive mechanism 61 that is supported by the X-axis drive mechanism 60 and raises and lowers the dispensing nozzle 57 in the Z-axis direction (vertical direction). Since each of the drive mechanisms 58, 59, and 60 includes a drive source (not illustrated), the dispensing nozzle 57 can be moved in the X direction, the Y direction, and the Z direction by these drive sources. Meanwhile, since a stepping motor of which the angle of a rotating shaft can be controlled is used as each of the drive sources (not illustrated) included in the dispensing apparatus 53 of this embodiment, each of the drive mechanisms 58, 59, and 60 can be accurately moved to a predetermined position that is instructed in advance. Further, the operations of these drive sources and the suction-discharge device 2 are controlled by operation signals transmitted from a dispensing control unit (not illustrated, the same shall apply hereinafter).

Furthermore, the base end portion of the suction-side tube 8 of the suction-discharge device 2 included in this embodiment is connected to a pressure-transmission water tank 62 that stores pressure-transmission water. The pressure-transmission water is liquid that is to be sucked and discharged by the suction-discharge device 2 included in this embodiment, and is liquid used to transmit pressure, which is generated by the operation of the syringe pump 18 when a dispensing operation is performed, to the dispensing nozzle 57. Functional water, such as ion-exchange water, electrolyzed water, or pure water, is mainly used as the pressure-transmission water. When a new suction-discharge assembly 48 is installed, the dispensing control unit activates the syringe pump 18, which is included in the suction-discharge device 2, to fill the respective tubes 8 and 9, the dispensing nozzle 57, and the pipette tip 33 with pressure-transmission water as a preparation operation before the dispensing of a sample.

As an operation for filling the respective tubes 8 and 9, the dispensing nozzle 57, and the pipette tip 33 with pressure-transmission water, first, the dispensing control unit rotationally moves the rotor 4 to a position where the suction-side tube 8 is opened and the discharge-side tube 9 is blocked. After that, the dispensing control unit moves the piston part 23 of the syringe pump 18 backward to suck pressure-transmission water from the pressure-transmission water tank 62. Next, the dispensing control unit rotationally moves the rotor 4 to a position where the discharge-side tube 9 is opened and the suction-side tube 8 is blocked. After that, the dispensing control unit moves the piston part 23 of the syringe pump 18 forward to discharge air that is filled in the tubes 8 and 9 and the syringe pump 18. Then, the dispensing control unit repeats the above-mentioned operation to fill the piping system of the suction-discharge device 2 with pressure-transmission water.

Figure 15A:
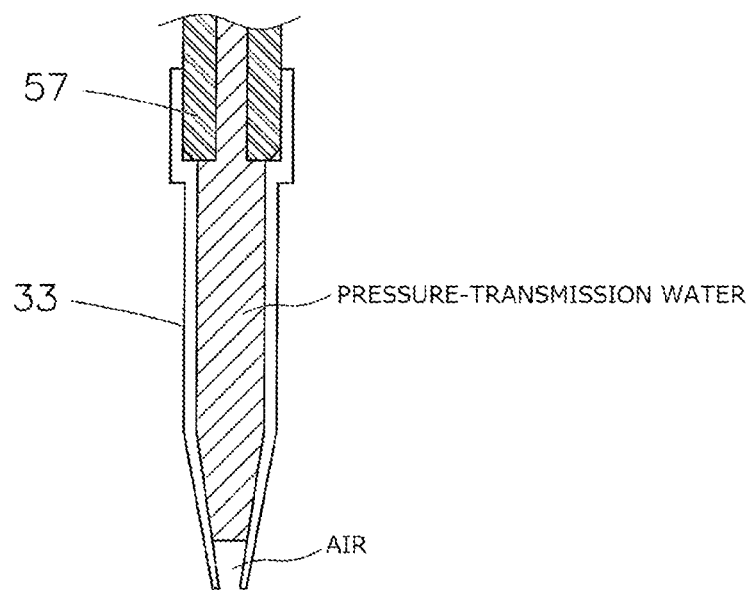
FIGS. 15(a) and 15(b) are cross-sectional views illustrating the internal state of a pipette tip when the dispensing apparatus of the invention sucks a sample.
Figure 15B:
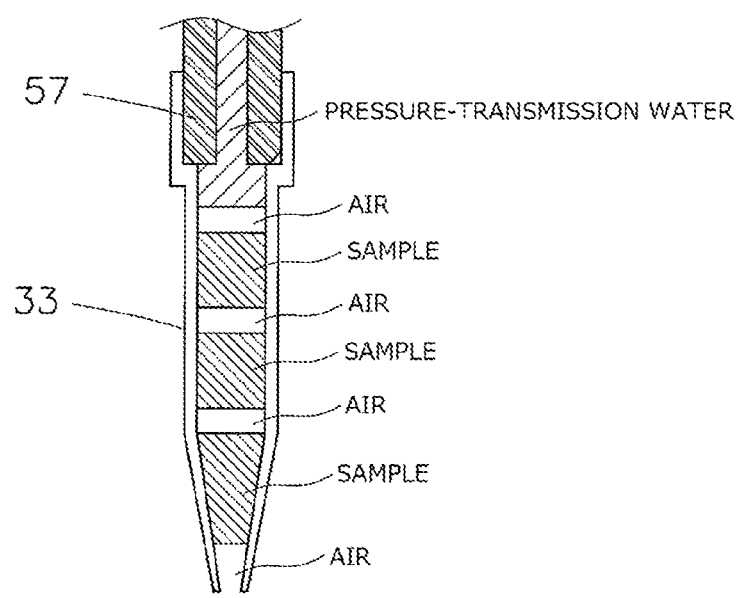

Next, a dispensing operation, which is performed by the dispensing apparatus 53 of this embodiment, will be described. Before the start of the dispensing operation, the dispensing control unit moves the piston part 23 of the syringe pump 18 of the suction-discharge device 2 backward to suck air from the tip of the pipette tip 33, which is filled with the pressure-transmission water, by a predetermined amount (see FIG. 15(a)). This is to prevent the pressure-transmission water and a sample from being mixed with each other, and the amount of air to be sucked is managed by the operation of the motor 19 that operates the piston part 23 of the syringe pump 18. Meanwhile, when this operation is performed, first, the dispensing control unit activates the motor 12 to rotationally move the rotor 4 of the suction-discharge device 2 to a position where the suction-side tube 8 is blocked and the discharge-side tube 9 is opened. Then, the dispensing control unit operates the nozzle transfer unit 58 to transfer the dispensing nozzle 57, on which the pipette tip 33 having sucked air is mounted, to a position immediately above the sample vessel 54. After that, the dispensing control unit lowers the dispensing nozzle 57 to a position where the tip of the pipette tip 33 is inserted into the sample stored in the sample vessel 54. Then, the dispensing control unit activates the motor 19 of the syringe pump 18 to move the piston part 23 backward and to suck the sample by a predetermined amount. When the suction of the sample is completed, the dispensing apparatus 53 operates the nozzle transfer unit 58 to raise the pipette tip 33 to a position above the sample vessel 54. After that, the dispensing control unit moves the piston part 23 of the syringe pump 18 of the suction-discharge device 2 backward again to further suck air from the tip of the pipette tip 33 by a predetermined amount. Then, the dispensing control unit lowers the dispensing nozzle 57 to a position where the tip of the pipette tip 33 gets into the sample stored in the sample vessel 54. After that, the dispensing control unit activates the motor 19 again to move the piston part 23 backward and to further suck the sample by a predetermined amount. The dispensing control unit repeatedly performs this operation preset times. Accordingly, a plurality of areas having a certain amount of sample, which are separated from each other by layers having a certain amount of air, are formed in the pipette tip 33 as illustrated in FIG. 15(b).

Next, the dispensing control unit transfers the pipette tip 33 to a position above a predetermined reaction vessel 55 and lowers the tip of the pipette tip 33 into a predetermined reaction well formed in the reaction vessel 55. When the operation for lowering the tip of the pipette tip 33 is completed, the dispensing apparatus 53 activates the motor 19 of the syringe pump 18 to supply the sample of which the amount corresponding to one area to the reaction well. When the supply of the sample to one reaction well ends, the dispensing control unit activates the nozzle transfer unit 58 and the suction-discharge device 2 to repeatedly perform an operation for supplying the sample, which is present in the pipette tip 33, to the next reaction well.

There is a case where the pipette tip 33 mounted on the dispensing nozzle 57 is replaced even in the dispensing apparatus 53. For example, in work, such as the sowing or pipetting of different kinds of cell suspension, trypsinization relating to subculturing operation, the concentration of phosphate buffered saline (PBS), and cells washing using the PBS, the replacement of the pipette tip 33 is performed to prevent a sample from being mixed with other specimens. In an operation for replacing the pipette tip 33, as in the above description, the pipette tip 33 is removed by the tip remover 39 and the mounting of a new pipette tip 33 of the tip rack 37 is performed.

When the mounting of a new pipette tip 33 is completed, the dispensing control unit activates the nozzle transfer unit 58 to move the dispensing nozzle 57, on which the pipette tip 33 is mounted, to a position above the tip remover 39, activates the syringe pump 18 of the suction-discharge device 2 to fill the pipette tip 33, which is newly mounted, with pressure-transmission water and then to suck air by a predetermined amount for the prevention of the mixing of the pressure-transmission water and a sample. Next, for the suction of a sample, the dispensing control unit activates the nozzle transfer unit 58 to move the dispensing nozzle 57 and the pipette tip 33 toward the sample vessel 54. In this way, the dispensing apparatus 53 of this embodiment can automatically perform work for accurately dispensing a large amount of sample by successively performing the replacement of a disposable pipette tip 33, the suction of a sample, and the discharge of the sample.

Meanwhile, the dispensing apparatus 53 of this embodiment has been provided with one dispensing nozzle 57, but can also be provided with a plurality of dispensing nozzles 57. In this case, it is preferable that the dispensing nozzles 57 are arranged in accordance with the number of wells arrayed in the reaction vessel 55 as a dispensing target in the form of a lattice and a distance between the wells so that operations for sucking and supplying a sample by the plurality of dispensing nozzles 57 are simultaneously and efficiently performed. Further, it is preferable that the tip remover 39 and the tip rack 37 are disposed in accordance with the positions of the plurality of dispensing nozzles 57 so that the pipette tips 33 of the plurality of dispensing nozzles 57 can be simultaneously and efficiently replaced. Furthermore, if one suction-discharge device 2 is provided for each dispensing nozzle 57, the amount of a sample to be dispensed for each dispensing nozzle 57 can be accurately controlled. According to the above-mentioned structure, time taken for work for dispensing a sample can be shortened without the deterioration of the accuracy of the amount of a sample to be dispensed.

Figure 16:
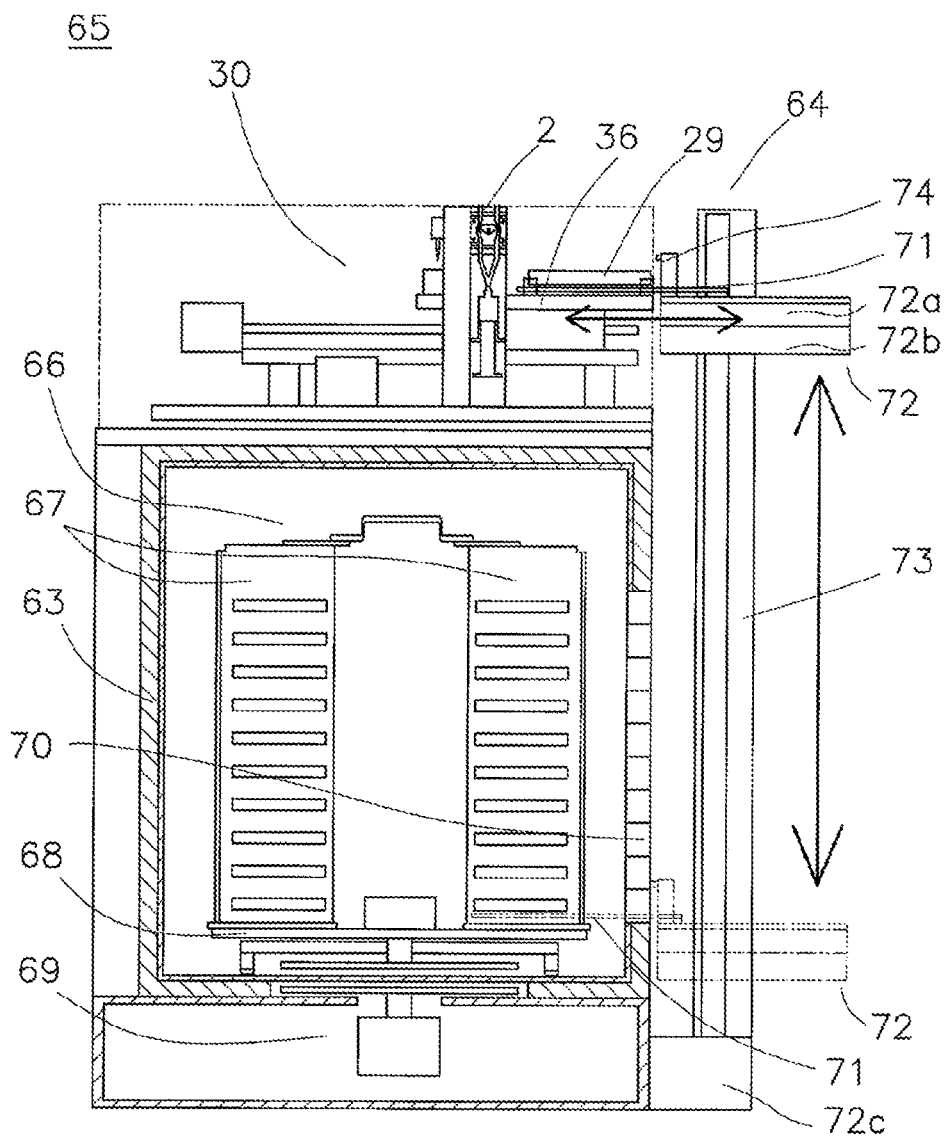
FIG. 16 is a cross-sectional view illustrating the outline of an automatic culture system of the invention.

Next, an automatic culture system 65 in which the culture medium replacement apparatus 30 having the structure illustrated in FIG. 11 including the suction-discharge device 2 of the invention is combined with a culture apparatus 63 including a transport mechanism 64 for a vessel 29 will be described. FIG. 16 is a cross-sectional view illustrating the automatic culture system 65 of this embodiment. The culture apparatus 63 is generally also called an incubator, and includes a constant-temperature chamber 66 that stores vessels 29 receiving a plurality of samples as objects to be cultured or inspected, and publicly known means for maintaining environmental conditions, such as temperature, humidity, and carbon dioxide concentration. The culture apparatus 63 included in the automatic culture system 65 of this embodiment includes vessel racks 67 in which the vessel 29 is placed on each of a plurality of trays, a rack stage 68 on which the plurality of vessel racks 67 are radially placed, and a stage drive unit 69 that rotationally moves the rack stage 68 in a horizontal plane, in addition to a device (not illustrated) for maintaining an environment. A stepping motor of which the rotation angle of a rotating shaft can be accurately controlled is used as a drive source of the stage drive unit 69. The culture apparatus 63 included in the automatic culture system 65 of this embodiment further includes a plurality of shield plates 70 that shield openings used to carry the vessels 29 in and out. Meanwhile, the culture apparatus 63 of this embodiment is provided with a magnet coupling mechanism for transmitting the rotational driving force of the stage drive unit 69, which is disposed outside of the constant-temperature chamber 66, to the rack stage 68, which is disposed in the constant-temperature chamber 66, with a magnetic force. Further, when the automatic culture system 65 of this embodiment is disposed in a clean booth that is maintained in a sterile environment, contamination can be prevented to a higher degree. Particularly, since a sample can be automatically cultured without the intervention of a human body that is the most extreme contaminant source, it is particularly effective to dispose the automatic culture system 65 in a clean booth.

The transport mechanism 64 included in the automatic culture system 65 of this embodiment includes a finger 71 that supports the vessel 29 from below, and a finger drive unit 72 that supports the finger 71 and transfers the finger 71 to a predetermined position in a front-back direction. The finger drive unit 72 includes: a forward/backward drive unit 72a that supports the finger 71 and moves the finger 71 along a guide (not illustrated) in a left-right direction in FIG. 16, that is, in a forward direction and a backward direction; a turning drive unit 72b that supports the forward/backward drive unit 72a and turns the forward/backward drive unit 72a; and a raising/lowering drive unit 72c that supports the turning drive unit 72b and raises and lowers the turning drive unit 72b along a guide 73 in the vertical direction. The raising/lowering drive unit 72c can raise or lower the turning drive unit 72b to a position where the finger 71 can have access to the vessel 29 placed on the vessel stage 36 of the culture medium replacement apparatus 30 placed above the culture apparatus 63. Furthermore, a stepping motor of which the rotation angle of a rotating shaft can be accurately controlled is used as a drive source for each of the drive units of the finger drive unit 72. According to this structure, the finger drive unit 72 and the stage drive unit 69 can transfer the finger 71 and the vessel 29, which is supported by the finger 71, to a predetermined tray, which is previously stored in a control device provided in the automatic culture system 65, by an operation command that is transmitted from a control device (not illustrated).

Further, the raising/lowering drive unit 72c is provided with an engagement mechanism 74 that is engaged with an engagement hole formed at the shield plate 70 and is used to open/close the shield plate 70. The engagement mechanism 74 includes an engagement pin that is fixed to the raising/lowering drive unit 72c at a position above the finger 71 and is engaged with the engagement hole formed at the shield plate 70. The engagement mechanism 74 includes a mechanism that moves the engagement pin forward or backward, and a drive source of the mechanism, which moves the engagement pin forward or backward, is provided with a stepping motor that can adjust the feed of the engagement pin. To open the shield plate 70, first, the raising/lowering drive unit 72c is raised or lowered to a predetermined position and the engagement mechanism 74 then moves the engagement pin toward the engagement hole of the shield plate 70. When the engagement pin is inserted into the engagement hole and the engagement mechanism 74 and the shield plate 70 are engaged with each other, the raising/lowering drive unit 72c is raised to raise the engaged shield plate 70 and a shield plate 70 that is disposed above the shield plate 70. Accordingly, an opening through which the finger 71 can have access to the vessel rack 67 is opened. When the access of the finger 71 to the vessel rack 67 ends, the engagement mechanism 74 moves the engagement pin backward to the original position after the raising/lowering drive unit 72c is lowered to block the opening. Meanwhile, the fact that the finger 71 has access to the vessel rack 67 means an operation for placing the vessel 29, which is held by the finger 71, on a predetermined tray of the vessel rack 67, or an operation for raising the vessel rack 67, which is placed on the predetermined tray of the vessel rack 67, from below by the finger 71 and carrying the vessel rack 67 to the outside of the constant-temperature chamber 66.

Next, the operation of the automatic culture system 65 of this embodiment will be described. To replace a culture medium of the vessel 29 that is stored in the constant-temperature chamber 66 of the culture apparatus 63, first, the stage drive unit 69 rotationally moves the rack stage 68 to a position where a target vessel 29 faces a shield plate 70 so that the transport mechanism 64 can have access to the target vessel 29. Then, the raising/lowering drive unit 72c and the engagement mechanism 74 cooperate with each other to open the corresponding shield plate 70. After that, the transport mechanism 64 operates the finger drive unit 72 to support the vessel 29 on the finger 71 and to move the vessel 29 to the outside of the constant-temperature chamber 66, and is then lowered to block the shield plate 70. Subsequently, the transport mechanism 64 operates the raising/lowering drive unit 72c to raise the finger 71 to a position where the vessel 29 supported by the finger 71 can be placed on the vessel stage 36 included in the culture medium replacement apparatus 30. At this time, the culture medium replacement apparatus 30 activates the stage transfer unit 44 to move the vessel stage 36, which is disposed on the replacement stage 35, to a position where the finger can have access to the vessel stage 36 (see FIG. 11). When the vessel stage 36 is moved to a position where the finger 71 can have access to the vessel stage 36, the transport mechanism 64 operates the finger drive unit 72 to place the vessel 29, which is supported by the finger 71, on the vessel stage 36. When the placement of the vessel 29 is completed, the transport mechanism 64 waits until the operations for replacing a culture medium performed by the culture medium replacement apparatus 30 ends. Meanwhile, since the operations for replacing a culture medium, which are to be performed afterward by the culture medium replacement apparatus 30, are the same as the operations having been already described, the operations will be omitted here.

When the replacement of a culture medium ends, the culture medium replacement apparatus 30 activates the stage transfer unit 44 again to moves the replacement stage 35 to a position where the finger can have access to the vessel 29 placed on the vessel stage 36. When the vessel stage 36 is moved to a position where the finger 71 can have access to the vessel stage 36, the transport mechanism 64 operates the finger drive unit 72 to scoop the vessel 29, which is placed on the vessel stage 36, to support the vessel 29 on the finger 71, and to lower the vessel 29 to a position corresponding to a predetermined tray of a predetermined vessel rack 67. After that, as in the case of the previous time, the shield plate 70 is opened and the vessel 29 is placed on a predetermined tray of a predetermined vessel rack 67 disposed in the constant-temperature chamber 66. When the placement of the vessel 29 ends, the transport mechanism is lowered, lowers the shield plate 70, which has been raised, to block the opening and a transport operation ends. Further, the culture period of a sample ends, the automatic culture system 65 operates the culture apparatus 63 and the transport mechanism 64 to carry the target vessel 29 out from the constant-temperature chamber 66, to transport the vessel 29 to a predetermined delivery position, and to deliver the vessel 29 to the next step.

When the automatic culture system 65 of this embodiment is used as described above, work for replacing a culture medium for cells or the like, which are being cultured, can be automated without the use of hands. Accordingly, the burden of a worker can be reduced. Further, since hands do not need to be used, contamination can be prevented. Furthermore, since the replacement of a certain amount of culture medium is reliably and mechanically performed, a difference in the growth states of the respective samples caused by work for replacing a culture medium does not occur. Accordingly, stable culture can be performed. Meanwhile, the technical scope of the invention is not limited to the above-mentioned embodiments, and the invention may have various modifications without departing from the scope of the invention.

EXPLANATIONS OF LETTERS OR NUMERALS

2: suction-discharge device
3, 3': switching valve
4, 4': rotor
6a, 6b: roller
8: suction-side tube
9: discharge-side tube
15: tube fixing member 17a, 17b, 17c, 17d: pressing member
18: syringe pump
30: culture medium replacement apparatus
53: dispensing apparatus
63: culture apparatus
65: automatic culture system

The invention claimed is:

1. A switching valve comprising:
    a rotor that includes a pair of rollers rotatably mounted on both ends thereof;
    a rotor drive unit that rotationally drives the rotor;
    a pair of pressing members, each of the pair of pressing members being provided at a position where each of the pair of pressing members cooperates with each of the pair of rollers outside a revolution orbit of each of the pair of rollers revolving by rotation of the rotor; and
    a pair of tubes, each of the pair of tubes being disposed between the revolution orbit of each of the pair of rollers and each of the pair of pressing members,
    wherein a gap between each of the pair of pressing members and the revolution orbit of each of the pair of rollers is narrow, and a pair of pressing areas where the pair of rollers and the pair of pressing members cooperate with each other to press and block one or both of the pair of tubes is formed by revolution of the pair of rollers,
    the pair of rollers is rotationally movable among a position where the pair of tubes is both blocked, a position where only one of the pair of tubes is blocked, and a position where flows in the pair of tubes are both allowed,
    the pair of tubes is selectively blocked and opened from an outside by the pair of rollers and the pair or pressing members by the revolution of the pair of rollers,
    a rotation center axis of the rotor is disposed on a straight line connecting centers of rotation of the pair of rollers, and
    the pair of pressing members has the pair of pressing areas that is symmetrical with respect to a straight line passing through the center of rotation of the rotor and extending a vertical direction.

2. A suction-discharge device comprising:
    the switching valve according to claim 1;
    a syringe pump to which each of end portions of the pair of tubes is connected; and
    a pump drive unit that moves a piston part of the syringe pump forward or backward with respect to a cylinder part,
    wherein the pump drive unit cooperates with the rotor drive unit to allow a sample to flow in the pair of tubes.

3. A culture medium replacement apparatus comprising:
    the suction-discharge device according to claim 2.

4. A dispensing apparatus comprising:
    the suction-discharge device according to claim 2.

5. An automatic culture system comprising:
    the culture medium replacement apparatus according to claim 3;
    a culture apparatus that receives a vessel, which receives a sample, in a constant-temperature chamber adjusted to a predetermined environment; and
    a transport mechanism that transports the vessel between the culture medium replacement apparatus and the culture apparatus.

6. An automatic culture system comprising:
    the dispensing apparatus according to claim 4;
    a culture apparatus that receives a vessel, which receives a sample, in a constant-temperature chamber adjusted to a predetermined environment; and
    a transport mechanism that transports the vessel between the culture medium replacement apparatus and the culture apparatus.

* * * * *